United States Patent
Lienkamp et al.

(10) Patent No.: US 10,259,915 B2
(45) Date of Patent: Apr. 16, 2019

(54) SYNTHESIS AND MICRO-/NANOSTRUCTURING OF SURFACE-ATTACHED CROSSLINKED ANTIMICROBIAL AND/OR ANTIBIOFOULING POLYMER NETWORKS

(71) Applicants: UNIVERSITÄTSKLINIKUM FREIBURG, Freiburg (DE); ALBERT-LUDWIGS-UNIVESITÄT FREIBURG, Freiburg (DE)

(72) Inventors: Karen Lienkamp, Gundelfingen (DE); Jakob Belardi, Nürnberg (DE); Peng Zou, Freiburg (DE); Ali Al-Ahmad, Freiburg (DE); Thorsten Steinberg, Mannheim (DE); Pascal Tomakidi, Freiburg (DE)

(73) Assignees: UNIVERSITATSKLINIKUM FREIBURG, Freiburg (DE); ALBERT-LUDWIGS-UNIVERSITAT FREIBURG, Freiburg (DE)

( * ) Notice: Subject to any disclaimer, the term of this patent is extended or adjusted under 35 U.S.C. 154(b) by 371 days.

(21) Appl. No.: 14/383,367

(22) PCT Filed: Mar. 8, 2013

(86) PCT No.: PCT/EP2013/054734
§ 371 (c)(1),
(2) Date: Sep. 5, 2014

(87) PCT Pub. No.: WO2013/132066
PCT Pub. Date: Sep. 12, 2013

(65) Prior Publication Data
US 2015/0025168 A1    Jan. 22, 2015

(30) Foreign Application Priority Data
Mar. 9, 2012  (EP) ..................... 12158742

(51) Int. Cl.
   *C08J 3/28*     (2006.01)
   *A01N 43/08*    (2006.01)
   (Continued)

(52) U.S. Cl.
   CPC ................ *C08J 3/28* (2013.01); *A01N 43/08* (2013.01); *A01N 43/10* (2013.01); *A01N 43/36* (2013.01);
   (Continued)

(58) Field of Classification Search
   CPC ...... C09D 5/1662; A01N 43/08; A01N 43/10; A01N 43/36; A61L 2/232; A61L 15/46;
   (Continued)

(56) References Cited

U.S. PATENT DOCUMENTS

2009/0123555 A1    5/2009  Sabaut-Heroguez et al.
2013/0338326 A1*  12/2013  Steinberg ............... A01N 25/10
                                                    526/268

FOREIGN PATENT DOCUMENTS

EP        2 000 803 A1    12/2008
WO    WO 2005/061110 A1    7/2005

OTHER PUBLICATIONS

International Search Report and Written Opinion dated Feb. 12, 2014 corresponding to International Patent Application No. PCT/EP2013/054734.
(Continued)

Primary Examiner — Robert S Walters, Jr.
(74) Attorney, Agent, or Firm — Squire Patton Boggs (US) LLP

(57) ABSTRACT

The present invention relates to substrates comprising a crosslinked network of covalently attached antimicrobial and/or antibiofouling polymers. The crosslinked network of antimicrobial and/or antibiofouling polymers acts highly efficiently against pathogens, e.g. bacteria and fungi. Both
(Continued)

Figure 1:
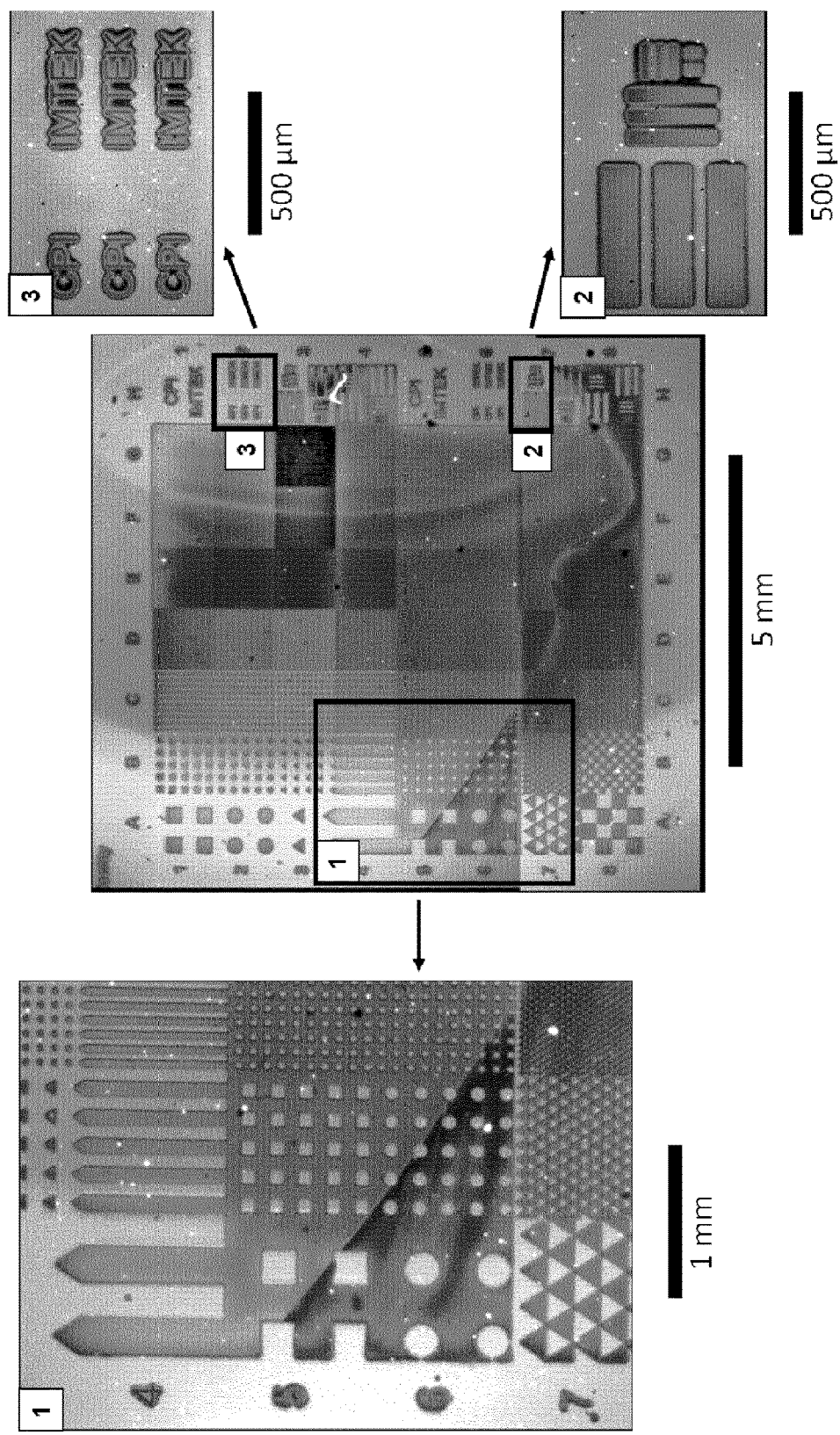

the antimicrobial and the antibiofouling cross-linked polymer networks are preferably better resistant to mechanical damage than simple surface-immobilized polymer monolayers. The antimicrobial and/or antibiofouling polymers of the crosslinked network are preferably obtained by ring opening metathesis polymerization (ROMP) and exhibit a molecular weight of preferably more than 30,000 or even 100,000 g mol$^{-1}$. The crosslinked network of antimicrobial and/or antibiofouling polymers is preferably covalently attached to the surface of a substrate, e.g. an implant, a medical device, medical equipment or a (tissue-supporting) biomaterial, etc. The present invention is also directed to uses of crosslinked networks of antimicrobial and/or antibiofouling polymers as defined herein, e.g. for coating a surface of a substrate, and to methods therefore.

11 Claims, 2 Drawing Sheets

(51) Int. Cl.
*A01N 43/10* (2006.01)
*A01N 43/36* (2006.01)
*A61L 29/08* (2006.01)
*C08G 61/08* (2006.01)
*C08G 61/12* (2006.01)
*A61L 2/232* (2006.01)
*A61L 27/34* (2006.01)
*A61L 27/54* (2006.01)
*A61L 29/16* (2006.01)
*A61L 31/10* (2006.01)
*A61L 31/16* (2006.01)
*A61L 15/46* (2006.01)
*C09D 5/16* (2006.01)
*C09D 5/14* (2006.01)

(52) U.S. Cl.
CPC ............... *A61L 2/232* (2013.01); *A61L 15/46* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *C08G 61/08* (2013.01); *C08G 61/12* (2013.01); *C09D 5/14* (2013.01); *C09D 5/1637* (2013.01); *C09D 5/1662* (2013.01); *A61L 2300/404* (2013.01); *A61L 2400/18* (2013.01); *C08G 2261/135* (2013.01); *C08G 2261/143* (2013.01); *C08G 2261/3342* (2013.01); *C08G 2261/418* (2013.01); *C08G 2261/76* (2013.01); *C08J 2345/00* (2013.01)

(58) Field of Classification Search
CPC ........ A61L 27/34; A61L 27/54; A61L 29/085; A61L 29/16; A61L 31/10; A61L 31/16; A61L 2300/404; A61L 2400/18; C08G 61/08; C08G 61/12; C08G 2261/135; C08G 2261/143; C08G 2261/3342; C08G 2261/418; C08G 2261/76
See application file for complete search history.

(56) References Cited

OTHER PUBLICATIONS

Semra Colak et al., "Dual-Functional ROMP-Based Betaines: Effect of Hydrophilicity and Backbone Structure on Nonfouling Properties," LANGMUIR, vol. 28, No. 1, Jan. 10, 2012, pp. 666-675, XP55036254.

* cited by examiner

SYNTHESIS AND MICRO-/NANOSTRUCTURING OF SURFACE-ATTACHED CROSSLINKED ANTIMICROBIAL AND/OR ANTIBIOFOULING POLYMER NETWORKS

The present invention relates to substrates comprising a crosslinked network of covalently attached antimicrobial and/or antibiofouling polymers. The crosslinked network of antimicrobial and/or antibiofouling polymers acts highly efficiently against pathogens, e.g. bacteria and fungi. Both the antimicrobial and the antibiofouling cross-linked polymer networks are preferably better resistant to mechanical damage than simple surface-immobilized polymer monolayers. The antimicrobial and/or antibiofouling polymers of the crosslinked network are preferably obtained by ring opening metathesis polymerization (ROMP) and exhibit a molecular weight of preferably more than 30,000 or even 100,000 g mol$^{-1}$. The crosslinked network of antimicrobial and/or antibiofouling polymers is preferably covalently attached to the surface of a substrate—preferably simultaneously to forming the network. The substrate is e.g. an implant, a medical device, medical equipment or a (tissue-supporting) biomaterial, etc. The present invention is also directed to uses of crosslinked networks of antimicrobial and/or antibiofouling polymers as defined herein, e.g. for coating a surface of a substrate, and to methods therefore.

Formation of biofilms in many areas of life and particularly in the field of medicine and implantology represent a problematic and sometimes even health or life threatening issue. Biofilms are agglomerates of microorganisms that adhere to a substrate usually in two stages. In stage I of the formation of a biofilm, bacteria bind reversibly to the surface. In stage II, the cells secrete binding molecules such as adhesion proteins that cause irreversible attachment to the surface. Once settled, the cell proliferates and forms colonies inside a peptidoglycan envelope and forms a mature biofilm. At this stage, the bacteria become inaccessible to antibacterial agents. One possibility to prevent such formation of biofilms is the use of antimicrobial and/or antibiofouling coatings. The role of such antimicrobial and/or antibiofouling coatings is to prevent a transition from stage I to stage II, while the role of antimicrobial coatings is further to prevent the transition from stage II to cell proliferation and biofilm formation by killing the adhering bacterial cells. Antimicrobial and/or antibiofouling surfaces have a wide range of applications, from coatings of medical devices to coatings of ship hulls and water pipelines (see e.g. Krishnan, S.; Weinman, C. J.; Ober, C. K., Advances in polymers for anti-biofouling surfaces. *Journal of Materials Chemistry* 2008, 18 (29), 3405-3413). One possibility to prevent the transition of bacteria from stage I to stage II is to minimize the adhesive forces between the cell and the surface.

Antibiofouling materials generally suitable for such purposes typically fall into two categories—so called non-fouling materials and fouling-release materials. In this context, it is important to recognize that it is energetically not advantageous for the bacterial cell to settle on a non-fouling coating due to the low surface energy gained. In turn, the force needed to detach a microorganism from a fouling-release coating is low enough to make the microorganism-surface binding reversible. Experimental evidence shows that certain materials exhibit such an antibiofouling activity, e.g. poly(ethylene glycol) (PEG). Several PEG based surfaces have been synthesized and have been shown to be significantly more resistant to protein absorption and cell adhesion than control surfaces (see Krishnan et al., (2008, vide supra); and Vladkova et al., *Journal of the University of Chemical Technology and Metallurgy* 2007, 42 (3), 239-256; Schilp et al., *Biointerphases* 2007, 2 (4), 143-150; Ma et al., *Advanced Materials* (Weinheim, Germany) 2004, 16 (4), 338-341; Du et al., *Biochimica et Biophysica Acta, Biomembranes* 1997, 1326 (2), 236-248; Park et al., *Biomaterials* 1998, 19 (7-9), 851-859; Wagner et al., *Biomaterials* 2004, 25 (12), 2247-2263; Fan et al., *Biomacromolecules* 2006, 7 (8), 2443-2448; Cheng et al., *Biomaterials* 2007, 28 (29), 4192-4199; Tugulu et al., *Biomacromolecules* 2008, 9 (3), 906-912; Page et al., *Journal of Materials Chemistry* 2009, 19 (23), 3819-3831)).

PEG-based materials are typical non-fouling materials with a low interfacial energy (5 mJ m$^{-2}$). Besides energy considerations, the dynamic movement of the PEG chains is believed to prevent pathogen adhesion (see e.g. Page et al., (2009), supra). For PEG, it has been shown that the polymer chain length and effects associated with molecular architectures are not relevant for the antibiofouling activity, as long as the surface is fully covered (see e.g. Krishnan et al. (2008, supra); and Ruehe et al., Polyelectrolyte brushes. *Advances in Polymer Science* 2004, 165 (Polyelectrolytes with Defined Molecular Architecture I), 79-150). It has been argued that the hydration layer near a hydrophilic surface (PEG chains on a surface contain 80 vol % of water, see Heuberger et al., *Langmuir* 2004, 20 (22), 9445-9448) is more important to prevent protein absorption than the steric repulsion effect that has been assumed for long PEG chains, although other opinions also exist (see e.g. Krishnan et al. (2008, supra); and Jiang et al., *Journal of Applied Polymer Science* 2006, 102 (3), 2324-2337). All in all, PEG coatings are currently the benchmark for antibiofouling surfaces, as they were shown to remain pristine even after four weeks at 37° C. in PBS buffer. The drawback of PEG, however, is that it degenerates oxidatively, which significantly reduces its antifouling activity and limits its applicability. Hence, alternatives are needed to either replace PEG or to support the properties of PEG to provide a longer antifouling activity.

In this context, polyzwitterions as another class of antibiofouling polymers have been discovered in the recent years. They have an equal number of negatively and positively charged moieties per repeat unit. Examples for such zwitterionic polymers are poly(phosphorylcholines) poly (sulfobetaines), and poly(carboxybetaines). Like PEG, these materials are extremely hydrophilic due to the association of large amounts of water around the charged groups. Unlike polyelectrolytes, polyzwitterions do not perturb the hydrogen-bonded network of water near the surface, which is thought to prevent protein adsorption and biofouling (see e.g. Kitano et al., *Journal of Colloid and Interface Science* 2005, 282 (2), 340-348; Kitano et al., *Langmuir* 2005, 21 (25), 11932-11940; Chen et al., *Langmuir* 2006, 22 (6), 2418-2421; Kitano et al., *Journal of Colloid and Interface Science* 2007, 313 (2), 461-468). Zwitterionic polymers were also found to have excellent biocompatibility towards fibroblasts and platelets (see e.g. Tada et al., *Macromolecular Bioscience* 2009, 9 (1), 63-70;) and help to reduce surface friction (see Kitano et al., *Colloids and Surfaces B-Biointerfaces* 2009, 74 (1), 350-357;), protein adsorption, mammalian cell adhesion, and biofilm formation (see e.g. Zhang et al., *Langmuir* 2006, 22 (24), 10072-10077; and Cheng et al., *Biomaterials* 2007, 28 (29), 4192-4199). Other less common hydrophilic polymers that prevent biofouling are poly(oxazolins) and poly(saccharides). It was shown that poly(2-methyl-2-oxazoline) grafted on poly(L-lysine) backbones were as efficiently antibiofouling as PEG grafted on poly(L-lysine) (see e.g. Konradi et al., *Langmuir* 2008, 24 (3), 613-616; and Pidhatika et al., *Chimia* 2008, 62 (4), 264-269). Chitosan and the oligosaccharides that make up the glycocalix of eukaryotic cells are also known for their antifouling properties and have been used as antibiofouling materials (see e.g. Holland et al *Nature* 1998, 392 (6678), 799-801). Examples include maltose dendrons on poly(vinyl amine), which prevent platelet adhesion (see e.g. Zhu et al., *Biomacromolecules* 2006, 7 (4), 1036-1041).

Hydrophobic surfaces like poly(dimethysiloxane), on the other hand, are fouling-release surfaces (see Krishnan et al., (2008, supra)) Another example of hydrophobic coatings are diamond-like carbon films. Due to their antifouling properties combined with their inertness, low frictional coefficient and high wear resistance, they have been used as coatings for stents or joint replacements (see e.g. Page et al., (2009, supra); and Liu et al., *Colloids and Surfaces B-Biointerfaces* 2008, 61 (2), 182-187). "Self-cleaning" super-hydrophobic surfaces, a combination of fluorinated polymers and hierarchical surface topologies, also prevent pathogen adhesion (see e.g. Genzer et al., *Biofouling* 2006, 22 (5), 339-360; and Krishnan et al., *Biomacromolecules* 2006, 7 (5), 1449-1462.). The idea of hierarchically structured surfaces has also been used in the design of shark skin-like surfaces from PDMS (see e.g. Schumacher, J. F.; Estes, T. G.; Callow, M. E.; Wendt, D. E.; Carman, M. L.; Wilson, L. H.; Brennan, A. B., Shark inspired non-toxic coatings for non-fouling marine applications. *Abstracts of Papers of the American Chemical Society* 2005, 230, 618-POLY.).

In contrast thereto, antimicrobial surfaces typically kill airborne or solution-borne pathogens upon contact. In this context, two general approaches are known in the art. According to one approach, a material is loaded with an antimicrobial component that is gradually leached to its destination. Alternatively, the surface itself is made from a material that is intrinsically antimicrobial.

Leaching antimicrobial materials according to the first approach, however, exhibit several intrinsic problems. First, they contaminate their surroundings; second, they are exhausted once the active agent has leached completely; and third, the dosing of the leachable component is non-linear and may be thus less efficient at some point of time even if the leachable component is still detectable at the surface of a material. Many materials used today in clinical settings are based on such leaching materials in lack of a better alternative. Examples of commercially available products with such leachable components contain e.g. the antimicrobial molecule triclosan, light-activated antimicrobial agents, or silver ions (see e.g. Page et al. (2009, supra)). Non-leaching surfaces can be obtained from intrinsically antimicrobial polymers, which is advantageous as polymers are easy to process and functionalize. Such polymers also can be blended with the plastic of a device, coatedpainted on surfaces, or covalently attached to surfaces such as glass, polymers or metals. Klibanov and coworkers have developed antimicrobial surfaces based on substituted poly(ethyleneimine) (PEI) and poly(vinylpyridine) (PVP). Other groups reported PVP-based, poly(diallyldimethylammonium)-based, poly(butylmethacrylate-co-amino-ethyl methyl-acrylate) as well as poly(2-(dimethyl-amino)-ethyl methacrylate)-based surfaces that were obtained either by "grafting from" or "grafting onto" approaches, or by film formation of antimicrobially functionalized latex particles (see e.g. Tiller et al., *Proceedings of the National Academy of Sciences of the United States of America* 2001, 98 (11), 5981-5985; Tiller et al., *Biotechnology and Bioengineering* 2002, 79 (4), 465-471; Lin et al., *Biotechnology Letters* 2002, 24 (10), 801-805; Lin et al., *Biotechnology and Bioengineering* 2003, 83 (2), 168-172; Lin et al., *Biotechnology Progress* 2002, 18 (5), 1082-1086; Park et al., *Biotechnology Progress* 2006, 22 (2), 584-589; Milovic et al., *Biotechnology and Bioengineering* 2005, 90 (6), 715-722; Cen et al., *Langmuir* 2003, 19 (24), 10295-10303; Cen et al., *Journal of Biomedical Materials Research Part A* 2004, 71A (1), 70-80; Hu et al., *Biotechnology and Bioengineering* 2005, 89 (4), 474-484; Fuchs et al., *Angewandte Chemie-International Edition* 2006, 45 (40), 6759-6762; Thome et al., *Surface & Coatings Technology* 2003, 174, 584-587; Madkour et al., *Langmuir* 2009, 25 (2), 1060-1067; Lee et al., *Biomacromolecules* 2004, 5 (3), 877-882; Huang et al., *Biomacromolecules* 2007, 8 (5), 1396-1399; and Murata et al., *Biomaterials* 2007, 28 (32), 4870-4879). While the mechanism of action of natural antimicrobial peptides (AMPs) and of antimicrobial polymers in solution is meanwhile partially understood the mechanism by which surface-bound polymers kill pathogens is still under debate.

In the last few years, significant progress has been made in the development of synthetic mimics of antimicrobial peptides (SMAMPs). As discussed in a review by Lienkamp and Tew (see Lienkamp and Tew, *Chem. Eur. J.* 2009, 15, 11784-11800), SMAMP design has evolved from structurally rigid, peptide-like molecules towards increasingly less-confined molecular architectures, some of which perform even better than their natural archetypes. Access to such synthetic SMAMPs may open up new applications, for example in the materials area, where bacterial infections from medical plastics are a current critical problem in our hospitals as discussed above. Synthetic polymers can be obtained easily and in large quantities while still presenting facial amphiphilicity and positive charge, the important features of antimicrobial peptides (AMPs). In this context, facially amphiphilic polymers typically contain a hydrophobic and a hydrophilic charged group on the same repeat unit. Although there have been several recent reports of polymeric SMAMPs, their overall activities and selectivities remain far from optimal.

Several approaches in this regard, however, have been reported e.g. in Gstrein et al. (see US 2008/251460 A1), which shows biocidal polymers based on poly(norbornene) derivatives. Such polymers, however, are statistic copolymers of a cationic and a hydrophobic repeat unit. Such statistic poly(norbornene) derivatives, even though showing biocidal activity, cannot be considered as selective for pathogens, as they cannot be fine tuned with regard to their local amphiphilicity.

Improved antimicrobial polymers with high selectivity for bacteria have furthermore been discussed in Lienkamp et al. (see Lienkamp et al., *J. Am. Chem. Soc.* 2008, 130, 9836; and Gabriel et al., *Chem. Eur. J.*, 2009, 15, 433) and in WO 2010144386 A2 by Lienkamp et al. This approach requires presence of facially amphiphilic repeat units, which is not the case in the static copolymers of Gstrein et al.

Notably, many publications also report a dependency of antimicrobial activity of AMPs and SMAMPs on molecular weight. In this context, the prior art shows molecular weight ranges of from a few hundred g mol$^{-1}$ to about 50,000 g mol$^{-1}$ and in any case below 100,000 g mol$^{-1}$ (see also Tew et al., US 2010/317870 A1). Most of the studies mentioned investigated two or more compounds with different molecular weights for each polymer type. Lienkamp and Tew (2009, supra) discuss how molecular weight in the known ranges affects SMAMP properties. However, the molecular weight dependence of antimicrobial activity that has been discussed so far merely relates to the activity of antimicrobial molecules in solution. Since the mechanism of antimicrobial action is different when immobilized on a surface, other molecular weight dependencies may apply, if an antimicrobial activity can be detected at all.

It has now been found by Lienkamp et al. (unpublished data) that antimicrobial polymers with a molecular weight of more than 100.000 g mol$^{-1}$ can be covalently attached to a surface. It also has been found by Lienkamp et al. that these surface-immobilized polymers were highly active against bacteria, which emphasizes the fact that the mechanism in solution and on surfaces must be different. Lienkamp et al. also showed that a high molecular weight polymer is necessary for their particular method of surface immobilization, as lower weight polymers do not sufficiently adhere to the surface, presumably due to too few covalent bonds per molecule. Even though such covalently attached antimicrobial polymer monolayers as found by Lienkamp et al. appear to exhibit highly advantageous properties, they are quite sensitive to mechanical damages, and the overall film thickness is limited to twice the radius of gyration of a single polymer coil.

Even though several amphiphilic molecules have been discussed already to be a promising basis for the development of future antimicrobial materials, it appears to be very difficult to draw general conclusions concerning the dependency of biological activity on specific molecular structure and molecular weight. Every new polymer system that has been designed to capture the key features for antimicrobial activity (positive charge and a hydrophobic group) must be fine tuned experimentally to get the other important parameters (global chargehydrophobicity balance, the local amphiphilicity, backbone effects, molecular weight effects, tacticity effects) right. Otherwise, the polymer may be inactive or toxic, as the balance between the two functionalities (hydrophobic and cationic) is a very subtle one and to date cannot be calculated or otherwise predetermined.

Furthermore, one has to point out that solution activity and surface activity are two entirely different things, and one cannot simply "translate" a minimum inhibitory concentration in solution into an antimicrobial activity on a surface. Apart from different mechanisms of action in these two cases other parameters besides molecular structure also play a role when a polymer chain is immobilized on a surface. These include the amount of surface coverage, the resulting surface roughness, the mechanical stability of the surface, stability of the surface-polymer linker, to name but a few. Thus, a system which provides a highly active antimicrobial polymer that can be easily immobilized on a variety of surfaces in variable thicknesses and with sufficient mechanical robustness is highly desirable. Ideally, such a system could be combined with an antibiofouling moiety to obtain a bifunctional surface that can prevent biofilm formation by interrupting the biofilm formation process at various levels. Additionally, for uses such as coatings on implants, it is essential that the coating vanishes once the wound has healed and the coating has performed a task. Thus, such a coating is preferentially also degradable.

Bearing the above in mind, there still remains the need to provide efficient antimicrobial and/or antibiofouling polymers, which avoid at least some of the above mentioned disadvantages, such as leaching out or a considerable loss of activity after short time limits of application.

This object is solved by the subject matter of the attached claims. The different embodiments as described in the following can be suitably combined with each other.

Preferably, according to a first embodiment, the underlying object is solved by a crosslinked polymer network of either antimicrobial or antibiofouling polymers of any of (antimicrobial) formulae (Ia), (Ib), (Ic), (Id), (Ie) and/or (If), or (antibiofouling) formulae (IIa), (IIb), (IIc), (IId) and/or (IIe) as defined below, by combinations thereof as well as by co-polymers and blends thereof. The crosslinked network is preferably covalently attached to a surface of a substrate, e.g., an implant, a medical device or medical equipment, etc. Such a surface or substrate and uses thereof does not impair the antimicrobial and/or antibiofouling activity of the herein defined antimicrobial or antibiofouling polymers. The antimicrobial and/or antibiofouling polymers of the inventive cross-linked polymer network exhibit a molecular weight of more than 1,000, 2,000 or 3,000 g mol$^{-1}$, more than 10,000 g mol$^{-1}$, preferably more than 30,000 g mol$^{-1}$, even more preferably more than 50,000 g mol$^{-1}$ or more than 75,000 g mol$^{-1}$. Advantageously, such antimicrobial and/or antibiofouling polymers exhibit a molecular weight of more than 100,000 g mol$^{-1}$, most preferably a molecular weight in a range as further defined below. Preferably, covalent attachment to the surface of the substrate and crosslinking of the network has been carried out simultaneously.

In contrast to previously developed polymer monolayers of antimicrobial polymers, these cross-linked polymer networks from antimicrobial and/or antibiofouling polymers as described herein have the following particular advantages:

More reliable surface coverage and higher mechanical robustness. As the polymer networks are not limited in their thickness, they tolerate the presence of surface imperfections better than the monolayers, so that homogeneously covered surfaces can be also obtained on "real life" samples. The additional cross linking within the network further stabilizes the layer and improves the substrate adhesion.

Tunable thickness of the surface coating. While the monolayer thickness is limited to twice the radius of gyration of the polymer used, cross-linked surface attached networks can be produced in any thickness from tens of nanometers to millimeters. With a prolonged exposure of the antimicrobial polymers developed previously, a maximum film thicknesses of up to 50 nm for a 100,000 g mol$^{-1}$ polymer could be produced as a monolayer, wherein the thickness of the monolayer was mainly determined by the high molecular weight of the antimicrobial polymers of at least 100,000 g mol$^{-1}$.

Higher relative surface area. As the cross-linked network invariably has pores of certain dimensions, the surface has a higher relative surface area compared to the monolayer. This allows further functionalization of the polymer network to include other chemical functionalities, e.g. antimicrobial on antibiofouling or vice versa, or even different types of antibiofouling polymers onto each other.

On these cross-linked polymer networks from antimicrobial polymers, antibiofouling polymers may be bound and vice versa. The present inventors specifically showed that a "grafting onto" reaction, which did not work well on the monolayer, was feasible on the cross-linked network.

Furthermore, the synthetic method used for production of the antimicrobial and/or antibiofouling polymers as defined herein allows for a better control over the target molecular weight and polydispersity of the synthesized polymers, in particular providing polymers having a defined molecular weight of more than 1,000 g mol$^{-1}$ or of even more than 10,000 g mol$^{-1}$ or even 100,000 g mol$^{-1}$, preferably of more than 30,000 g mol$^{-1}$. The antimicrobial and/or antibiofouling polymers as defined herein were designed by the present inventors through advanced polymer design and synthesis methods. In particular, for example, a ring opening metathesis polymerization (ROMP) platform was utilized that allows synthesis of both low and high molecular weight antimicrobial and/or antibiofouling polymers. These antimicrobial and/or antibiofouling polymers employ a minimum number of norbornene-based building blocks and/or enable easy and independent variation of hydrophobic and hydrophilic groups in the repeat units and/or along the polymeric backbone. This allows fine-tuning and selecting desirable properties (e.g., antimicrobial activity and cell selectivity) of these polymers.

Particularly, the underlying problem is solved according to a first embodiment by a substrate comprising preferably covalently attached a cross-linked network of antimicrobial polymers or by a cross-linked network of antimicrobial polymers as such, the antimicrobial polymers of the network comprising a molecular weight of more than 1,000 g mol$^{-1}$, preferably more than 30,000 g·mol-1, and as a repeat unit a structure according to at least one of formulae (Ia), (Ib), (Ic), (Id) and/or (Ie), or a combination thereof:

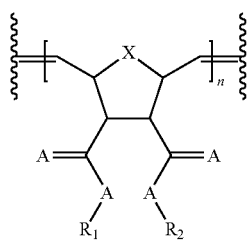

(Ia)

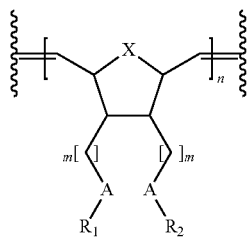

(Ib)

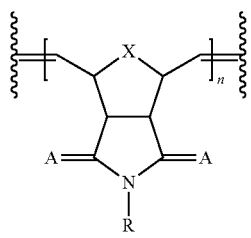

(Ic)

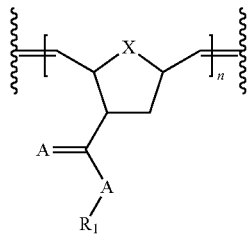

(Id)

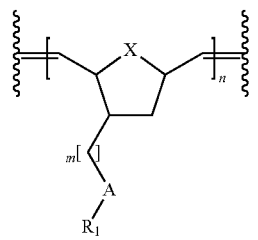

(Ie)

wherein preferably

A is selected independent from each other from any of O, S, or NH, preferably O;

R is selected from $(CH_2)_p$ $N^+(R_6)_3$
  wherein
    $R_6$ is selected from H or is (preferably independent from each other) an uncharged hydrophobic or hydrophilic group; and
    p is an integer selected from a range of about 1 to about 10;

$R_1$ is a hydrophilic group, preferably carrying a positive charge, which is even more preferably protected by a protecting group;

$R_2$ is a hydrophobic group;

X is selected from any of $CH_2$, $CH_2CH_2$, O, S, N—$R_3$, P—$R_3$, or C=C($R_4R_5$);
  wherein
    $R_3$, $R_4$, and/or $R_5$ is selected independent from each other from H or a hydrophobic or a hydrophilic group;

n is an integer selected from a range of about 10 to about 2500;

m is an integer selected from a range of about 0 to about 20; and wherein the net charge of all positive and negative charges per repeat unit of any of formulae (Ia), (Ib), (Ic), (Id) and/or (Ie) in its deprotected form is >0.

Such an antimicrobial polymer is termed an "amphiphilic" polymer.

Preferably, n is an integer selected from about 10 to about 2500, from about 30 to about 2500, from about 50 to about 2500, from about 100 to about 2500, or from about 150 to about 2500, preferably from about 250 to about 2500, for example from about 250 to about 750, from about 500 to about 1000, from about 750 to about 1250, from about 1000 to about 1500, from about 1250 to about 1700, from about 1500 to about 2000, from about 1750 to about 2250, or from about 2000 to about 2000, or from about 250 to about 1500 to about, from about 1000 to about 2500; etc., or even more preferably comprises a range formed by any of two of the above values, most preferably e.g. from about 100 to about 2500, or from about 150 to about 2500, preferably from about 250 to about 2500.

Likewise preferably, m is an integer selected from about 0 to about 20, from about 1 to about 20, from about 2 to about 20, from about 0 to about 15, from about 1 to about 15, from about 2 to about 15, from about 0 to about 10, most preferably from about 1 to about 10, from about 2 to about 10, from about 0 to about 5, from about 1 to about 5, from about 2 to about 5, from about 3 to about 5, or from about 4 to about 5, or may be selected from any of the values 0, 1, 2, 3, 4, 5, 6, 7, 8, 9, 10, 11, 12, 13, 14, 15, 16, 17, 18, 19 or 20, or even more preferably comprises a range formed by any of two of the above values.

Likewise preferably, p is an integer selected from about 1 to about 10, from about 2 to about 10, from about 3 to about 10, from about 4 to about 10, from about 5 to about 10, from about 1 to about 5, from about 2 to about 5, from about 3 to about 5 or from about 4 to about 5, or may be selected from any of the values 1, 2, 3, 4, 5, 6, 7, 8, 9 or 10, or even more preferably comprises a range formed by any of two of the above values.

In the context of the present invention the terms "hydrophobic group" or "hydrophobic moiety" preferably refer to a group having a property such that an affinity of the (hydrophobic) group for water is low (e.g. being non-polar). Non-limiting examples of hydrophobic groups or moieties as used according to the present invention may comprise or consist of linear, branched, cyclic, substituted, unsubstituted, saturated, partially saturated and/or unsaturated compounds having 1 to 30 or more carbon atoms ($C_1$-$C_{30}$), more preferably having 1 to 30 carbon atoms ($C_1$-$C_{30}$), even more preferably having 1 to 10 or more carbon atoms ($C_1$-$C_{30}$), and most preferably having 1 to 12 or more carbon atoms ($C_1$-$C_{12}$). Examples are preferably selected from such alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl-groups, more preferably selected from linear, branched, cyclic, substituted and unsubstituted, saturated, partially saturated and/or unsaturated ($C_1$-$C_{30}$) alkyl, ($C_1$-$C_{30}$) alkenyl, ($C_1$-$C_{30}$) alkynyl, or ($C_1$-$C_{30}$) aryl groups, ($C_1$-$C_{30}$) heteroalkyl, ($C_1$-$C_{30}$) heteroalkenyl, ($C_1$-$C_{30}$) heteroalkynyl, ($C_1$-$C_{30}$) heteroaryl, or ($C_1$-$C_{30}$) heteroarylalkyl groups, or from linear, branched, cyclic, substituted, unsubstituted, saturated, partially saturated and/or unsaturated ($C_1$-$C_{30}$) cycloalkyl, ($C_1$-$C_{30}$) cycloalkenyl, ($C_1$-$C_{30}$) cycloalkynyl, ($C_1$-$C_{30}$) heterocycloalkyl, and ($C_1$-$C_{30}$) heterocycloalkenyl-groups, preferably having 1, 2, 3, or 4, 1 to 3, 1 to 4, or even more rings. A hydrophobic group as defined herein may additionally contain some hydrophilic groups or substituents insofar as the hydrophobic character of the hydrophobic group is not outweighed. In further variations, a hydrophobic group as defined according to the present invention may include substituted silicon atoms and/or fluorine atoms. The hydrophobic moieties may be linear, branched, or cyclic.

In the context of the present invention, a $C_1$-$C_{30}$ group as defined above, e.g. any of the above defined ($C_1$-$C_{30}$) alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl groups, may preferably include or be selected from a $C_1$-$C_{30}$, $C_1$-$C_{25}$, $C_1$-$C_{20}$, $C_1$-$C_{15}$, $C_1$-$C_{12}$, $C_1$-$C_6$, $C_6$-$C_{30}$, $C_{12}$-$C_{30}$, $C_{13}$-$C_{30}$, $C_{15}$-$C_{30}$, $C_{20}$-$C_{30}$ or a $C_{25}$-$C_{30}$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, or $C_{30}$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group, or an alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group selected from any range formed by any of two of the above values.

According to one exemplary aspect a $C_1$-$C_{12}$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group may preferably include or be selected from a $C_1$-$C_{12}$, $C_2$-$C_{12}$, $C_3$-$C_{12}$, $C_4$-$C_{12}$, $C_5$-$C_{12}$, $C_6$-$C_{12}$, $C_7$-$C_{12}$, $C_8$-$C_{12}$, $C_9$-$C_{12}$, $C_{10}$-$C_{12}$, $C_{11}$-$C_{12}$, $C_1$-$C_{11}$, $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, or a $C_1$-$C_2$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group, or may be selected from a $C_1$, $C_2$, $C_3$, $C_4$, $C_5$, $C_6$, $C_7$, $C_8$, $C_9$, $C_{10}$, $C_{11}$, or a $C_{12}$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group, or from any range formed by any of two of the above values. Exemplary ($C_1$-$C_6$) alkyl groups include methyl, ethyl, n-propyl, isopropyl, n-butyl, isobutyl, pentyl, isopentyl, hexyl, etc. Of course, other ($C_1$-$C_6$) alkyl groups will be readily apparent to those of skill in the art given the benefit of the present disclosure. Exemplary ($C_1$-$C_6$) alkenyl groups include ethenyl, 1-propenyl, 1-butenyl, 2-butenyl, 1,3-butadienyl, 1-penten, 2-penten, 2-methyl-3-buten, 2-methyl-3-penten, 3-methyl-2-penten, 4-methyl-3-penten, etc. Likewise, other ($C_1$-$C_6$) alkenyl groups will be readily apparent to those of skill in the art given the benefit of the present disclosure. The same applies to alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl groups as defined above.

According to a specific aspect, the hydrophobic group of $R_2$, optionally the hydrophobic group of $R_3$, $R_4$, $R_5$ and/or $R_6$, of the antimicrobial polymer having as a monomeric repeat unit a structure according to any of formulae (Ia), (Ib), (Ic), (Id) and/or (Ie), may be selected from a $C_1$-$C_{12}$ or $C_1$-$C_6$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group as defined above, preferably from a linear or branched substituted or unsubstituted $C_1$-$C_{12}$ alkyl group as defined above, e.g., a linear or branched substituted or unsubstituted $C_1$-$C_{12}$ alkyl group or $C_1$-$C_6$ alkyl group.

According to one even more specific aspect, the hydrophobic group of $R_2$ of the antimicrobial polymer having as a monomeric repeat unit a structure according to any of formulae (Ia), (Ib), (Ic), (Id) and/or (Ie) may be selected from the group

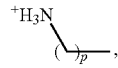

wherein p is an integer as defined above preferably selected from a range selected from 1-10, 1-9, 1-8, 1-7, 1-6, 1-5, 1-4, 1-3, 1-2, or preferably selected from a range selected from 1-10, 2-10, 3-10, 4-10, 5-10, 6-10, 7-10, 8-10, or 9-10, or preferably selected from 1, 2, 3, 4, 5, 6, 7, 8, 9, or 10 or preferably selected from any range formed by any of two of the above values.

Furthermore, the terms "hydrophilic group" or "hydrophilic moiety" as used according to the present invention preferably refer to a group having a property such that an affinity of the group for water is high (e.g., high polarity). Preferably, a hydrophilic group or moiety as defined herein carries a positive charge, which is even more preferably protected by a protecting group. Non-limiting examples of hydrophilic groups or moieties include hydroxyl, methoxy, carboxylic acids and ions and salts thereof, amides, amino, cyano, isocyano, nitrile, ammonium ions or salts, sulfonium ions or salts, phosphonium ions or salts, guanidinium, biguanidinium, imidazolium mono- and di-alkyl substituted amino groups, polyethylene glycols, glycosyl groups, sugars, epoxy groups, acrylates, sulfonamides, nitro, aminate, acrylamide, pyridinium, piperidine, pyrazole, pyrol, imidazole, azirine, aziridine, diaziridine, azetidine, azete, diazetidine, azolidine, phosopholane, phosphole, arsolane, arsole, imidazolidine, pyrazolidine, imidazolin, pyrazoline, oxazolidine, isoxazolidine, oxazole, oxazoline, isoxazole, isoxazoline, thiazolidin, isothiazolidin, thiazole, thiazolin, isothiazole, isothiazoline, triazole, dithiazole, furazan, oxadiazole, thiadiazole, tetrazole, piperazin, diazine, morpholin, oxazin, thiazin, triazin, tetrazine, zwitterions or amino acids, and combinations thereof, or from OP(O)(OCH$_2$CH$_2$N$^+$RRR)O$^-$, wherein each R is independently selected from H or an alkyl as defined herein. Further examples include poly(methylene) chains substituted with alcohol, carboxylate, acrylate, or methacrylate. Hydrophilic moieties may also include alkyl chains having internal amino or substituted amino groups, for example, internal —NH, —NC(O)R, or —NC(O)CH=CH$_2$-groups, wherein R is H or an alkyl as defined herein. Hydrophilic moieties may also include poly(caprolactone(s)), poly(caprolactone diol(s)), poly(acetic acid)(s), poly(vinyl acetates)(s), poly(2-vinyl pyridine)(s), cellulose ester(s), cellulose hydroxylether(s), poly(L-lysine hydrobromide)(s), poly(itaconic acid)(s), poly(maleic acid)(s), poly(styrenesulfonic acid)(s), poly(aniline)(s), or poly(vinyl phosphonic acid)(s), poly (zwitterions) or poly(aminoacids). A hydrophilic group may contain some hydrophobic groups or substituents insofar as the hydrophilic character of the group is not outweighed. Without being limited thereto, exemplary positively charged hydrophilic groups or moieties may be selected from ammonium ions or salts, sulfonium ions or salts, phosphonium ions or salts, guanidinium, biguanidinium, imidazolium mono- and di-alkyl substituted amino groups, etc.

According to one specific aspect, the hydrophilic group of R$_1$ of the antimicrobial polymer as defined above and having as a monomeric repeat unit a structure according to any of formulae (Ia), (Ib), (Ic), (Id) and/or (Ie) may include e.g. a group selected from ammonium ions, sulfonium ions, phosphonium ions, guanidinium, biguanidinium, imidazolium, and mono- and di-alkyl substituted amino groups, preferably an C$_1$-C$_{12}$ alkyl as defined above, comprising a group selected from ammonium ions, sulfonium ions, phosphonium ions, and mono- and di-alkyl substituted amino groups.

According to a particularly specific aspect in the antimicrobial polymer having as a monomeric repeat unit a structure according to any of formulae (Ia), (Ib), (Ic), (Id) and/or (Ie) as defined above, X is O, A is O and R$_2$ is a linear or branched C$_1$-C$_{12}$ alkyl group as defined above, e.g., a linear or branched C$_1$-C$_6$ alkyl group as defined above; and R$_1$ is

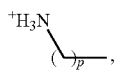

wherein p is an integer preferably selected from a range selected from 1-10, 1-9, 1-8, 1-7, 1-6, 1-5, 1-4, 1-3, 1-2, or preferably selected from a range selected from 1-10, 2-10, 3-10, 4-10, 5-10, 6-10, 7-10, 8-10, or 9-10, or preferably selected from 1, 2, 3, 4, 5, 6, 7, 8, 9, or 10 or preferably selected from any range formed by any of two of the above values.

According to an alternative specific aspect in the antimicrobial polymer having as a monomeric repeat unit a structure according to any of formulae (Ia), (Ib), (Ic), (Id) and/or (Ie) as defined above, X is CR$_7$R$_8$ as defined above, wherein R$_7$ and R$_8$ are preferably independent from each other selected from a hydrogen, or a C$_1$-C$_{12}$ alkyl or alkoxy group as defined above, most preferably a hydrogen; A is O; R$_2$ is a linear or branched C$_1$-C$_{12}$ alkyl group (e.g., a C$_1$-C$_6$ alkyl group); and R$_1$ is

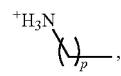

wherein p is an integer preferably selected from a range selected from 1-10, e.g. 1-9, 1-8, 1-7, 1-6, 1-5, 1-4, 1-3, 1-2, or preferably selected from a range selected from 1-10, e.g. 2-10, 3-10, 4-10, 5-10, 6-10, 7-10, 8-10, or 9-10, or preferably selected from 1, 2, 3, 4, 5, 6, 7, 8, 9, or 10 or preferably selected from any range formed by any of two of the above values.

According to a particularly preferred embodiment the underlying problem is solved by a substrate comprising preferably covalently attached a cross-linked network of antimicrobial polymers or by a cross-linked network of antimicrobial polymers as such, the antimicrobial polymers of the network comprising a molecular weight of more than 1,000 g mol$^{-1}$, preferably more than 30,000 g·mol-1, and as a repeat unit a structure according to formula (If):

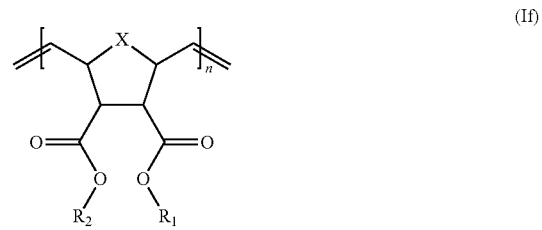

wherein preferably

X is selected from any of CH$_2$, CH$_2$CH$_2$, O, S, N—R$_3$, P—R$_3$, or C=C(R$_4$R$_5$), even more preferably as defined above;

R$_1$ is a hydrophilic group, preferably carrying a positive charge, which is even more preferably protected by a protecting group, more preferably a hydrophilic group as defined above;

R$_2$ is a hydrophobic group, preferably as defined above; and n is an integer selected from a range of about 10 to about 2500; and wherein the net charge of all positive and negative charges per repeat unit of formula (If) in its deprotected form is >0. Notably, the structure according to formula (If) represents a preferred structure according to formula (Ia).

The crosslinked network of antimicrobial and/or antibiofouling polymers is preferably covalently attached/bound to the surface of the substrate. In certain embodiments, the crosslinked network formed by the antimicrobial or antibiofouling polymers may include predefined breaking points.

The antimicrobial polymers of the crosslinked network structure comprising as a repeat unit a structure according to any of formulae (Ia), (Ib), (Ic), (Id), (Ie) and/or (If), or a combination thereof, preferably exhibiting a molecular weight of more than 1,000, 2,000 or 3,000 g mol$^{-1}$, of more than 10,000 g mol$^{-1}$, preferably of more than 30,000 g mol$^{-1}$, even more preferably more than 50,000 g mol$^{-1}$ or more than 75,000 g mol$^{-1}$. Advantageously, such antimicrobial and/or antibiofouling polymers of the crosslinked network exhibit a molecular weight of more than 100,000 g mol$^{-1}$, or even a molecular weight of at least 150,000 g mol$^{-1}$, a molecular weight of at least 200,000 g mol$^{-1}$, a molecular weight of at least 300,000 g mol$^{-1}$, or a molecular weight of at least 400,000 g mol$^{-1}$, a molecular weight in a range of about 10,000 g mol$^{-1}$ to about 1,000,000 g mol$^{-1}$, a molecular weight in a range of about 30,000 g mol$^{-1}$ to about 1,000,000 g mol$^{-1}$, a molecular weight in a range of about 50,000 g mol$^{-1}$ to about 1,000,000 g mol$^{-1}$, a molecular weight in a range of about 75,000 g mol$^{-1}$ to about 1,000,000 g mol$^{-1}$, a molecular weight in a range of about 10,000 g mol$^{-1}$ to about 1,000,000 g mol$^{-1}$, a molecular weight in a range of about 30,000 g mol$^{-1}$ to about 1,000,000 g mol$^{-1}$, a molecular weight in a range of about 50,000 g mol$^{-1}$ to about 1,000,000 g mol$^{-1}$, a molecular weight in a range of about 75,000 g mol$^{-1}$ to about 1,000,000 g mol$^{-1}$, a molecular weight in a range of about 100,000 g mol$^{-1}$ to about 1,000,000 g mol$^{-1}$, a molecular weight in a range of about 150,000 g mol$^{-1}$ to about 1,000,000 g mol$^{-1}$, a molecular weight in a range of about 200,000 g mol$^{-1}$ to about 1,000,000 g mol$^{-1}$, a molecular weight in a range of about 300,000 g mol$^{-1}$ to about 1,000,000 g mol$^{-1}$, a molecular weight in a range of about 400,000 g mol$^{-1}$ to about 1,000,000 g mol$^{-1}$, a molecular weight in a range of about 150,000 g mol$^{-1}$ to about 900,000 g mol$^{-1}$, a molecular weight in a range of about 200,000 g mol$^{-1}$ to about 800,000 g mol$^{-1}$, a molecular weight in a range of about 300,000 g mol$^{-1}$ to about 700,000 g mol$^{-1}$, a molecular weight in a range of about 300,000 g mol$^{-1}$ to about 700,000 g mol$^{-1}$, a molecular weight in a range of about 200,000 g mol$^{-1}$ to about 700,000 g mol$^{-1}$, a molecular weight in a range of about 150,000 g mol$^{-1}$ to about 700,000 g mol$^{-1}$, a molecular weight in a range of about 100,000 g mol$^{-1}$ to about 700,000 g mol$^{-1}$, a molecular weight in a range of about 750,000 g mol$^{-1}$ to about 700,000 g mol$^{-1}$, a molecular weight in a range of about 50,000 g mol$^{-1}$ to about 700,000 g mol$^{-1}$, a molecular weight in a range of about 30,000 g mol$^{-1}$ to about 700,000 g mol$^{-1}$, a molecular weight in a range of about 10,000 g mol$^{-1}$ to about 700,000 g mol$^{-1}$, most preferably a molecular weight in a range of about 30,000 g mol$^{-1}$ to about 1,000,000 g mol$^{-1}$, e.g. about 10,000 g mol$^{-1}$, about 30,000 g mol$^{-1}$, about 50,000 g mol$^{-1}$, about 75,000 g mol$^{-1}$, about 100,000 g mol$^{-1}$, about 150,000 g mol$^{-1}$, about 200,000 g mol$^{-1}$, about 300,000 g mol$^{-1}$, about 400,000 g mol$^{-1}$, about 500,000 g mol$^{-1}$, about 600,000 g mol$^{-1}$, about 700,000 g mol$^{-1}$, about 800,000 g mol$^{-1}$, about 900,000 g mol$^{-1}$, about 1,000,000 g mol$^{-1}$, or even more or may comprises a range formed by any of two of the above values.

As outlined above, the underlying problem is preferably solved by a substrate comprising preferably covalently attached a cross-linked network of antimicrobial polymers or by a cross-linked network of antimicrobial polymers as such, the antimicrobial polymers of the network comprising a molecular weight of more than 1,000 g mol$^{-1}$ and as a repeat unit a structure according to at least one of formulae (Ia), (Ib), (Ic), (Id) and/or (Ie), or a combination thereof, or preferably comprising as a structure a repeat unit a structure according to formula (If), all formulae as defined herein.

Hence, the cross-linked network of antimicrobial polymers may comprise either the same antimicrobial polymers, each polymer having as a repeat unit a structure according one of formulae (Ia), (Ib), (Ic), (Id) and/or (Ie), or preferably (If), or may comprise a combination of antimicrobial polymers different to each other each antimicrobial polymer having as a repeat unit a structure according one of formulae (Ia), (Ib), (Ic), (Id) and/or (Ie), or preferably (If).

Alternatively or additionally, the cross-linked network of antimicrobial polymers may comprise mixed antimicrobial polymers or copolymers, each of these mixed antimicrobial polymers or copolymers having more than one, e.g. two, three or more repeat units different to each other in one mixed antimicrobial polymer, the different repeat units showing a structure according one of formulae (Ia), (Ib), (Ic), (Id) and/or (Ie), or preferably (If). Such mixed antimicrobial polymers or copolymers may comprise either the same mixed antimicrobial polymers or different mixed antimicrobial polymers, e.g. mixed antimicrobial polymers having either identical, partially identical or different repeat units with regard to other mixed antimicrobial polymers, the repeat units showing a structure according one of formulae (Ia), (Ib), (Ic), (Id) and/or (Ie), or preferably (If).

According to a second embodiment, the underlying problem is solved by a substrate comprising preferably covalently attached a cross-linked network of antibiofouling polymers or by a cross-linked network of antibiofouling polymers as such, the antibiofouling polymers of the network comprising a molecular weight of more than 1,000 g mol$^{-1}$ and as a repeat unit a structure according to at least one of formulae (IIa), (IIb), (IIc), (IId) and/or (IIe), or a combination thereof:

(IIa)

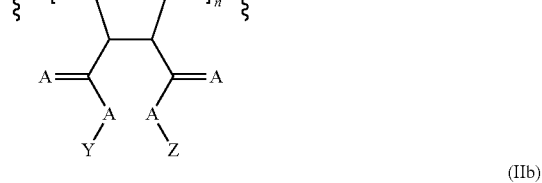

(IIb)

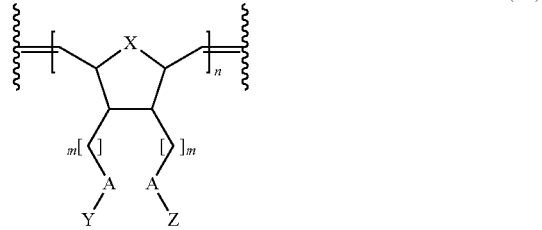

(IIc)

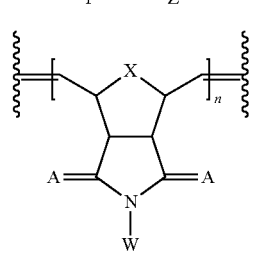

-continued (IId)

(IIe)

wherein preferably
A is selected independent from each other from any of O, S, or NH, preferably 0;
W is selected from any of $(CH_2)_qN^+(R_{11}R_{12}R_{13})$, or $(CH_2)_q O-PO_2^--(CH_2)_rN^+(R_{14}R_{15}R_{16})$, wherein $R_{11}$, $R_{12}$ is independent from each other an uncharged hydrophobic or hydrophylic group, and
  $R_{13}$ is selected from any of $(CH_2)_rCO_2^-$, $(CH_2)_rSO_3^-$, $(CH_2)_r-O-SO_3^-$, $(CH_2)_r-O-PO_3^-$, $(CH_2)_rPO_3^-$,
  $R_{14}$, $R_{15}$, $R_{16}$, is independent from each other H or an uncharged hydrophobic or hydrophilic group,
  q, r are integers, each independently selected from a range of about 1 to about 10;
X is selected from any of $CH_2$; $CH_2CH_2$; O; S; N—$R_9$; N—$R_{10}$; N—W; P—$R_9$; P—$R_{10}$; P—W; $N^+(R_9R_9)$; $N^+(R_9R_{10})$; $N^+(R_9W)$; $N^+(R_{10}W)$; $N^+(R_{10}R_{10})$; $N^+(WW)$; $C=CH_2$; $C=C(R_9R_9)$; $C=C(R_9R_{10})$, $C=C(R_9W)$; $C=C(R_{10}W)$, $C=C(R_{10}R_{10})$, $C=C(WW)$,
  wherein $R_9$ is selected preferably independent from each other from a hydrophobic or a hydrophilic group,
  $R_{10}$ is selected independent from each other from any of $(CH_2)_rCO_2^-$, $(CH_2)_rSO_3^-$, $(CH_2)_r-O-SO_3^-$, $(CH_2)_r-O-PO_3^-$, $(CH_2)_rPO_3^-$; and
  r is an integer selected from a range of about 1 to about 10;
Y is selected from W or any hydrophilic or hydrophobic group
Z is selected from W or any hydrophilic or hydrophobic group
n is an integer selected from a range of about 10 to about 2500;
m is an integer selected from a range of about 0 to about 20; and
wherein the net charge of all positive and negative charges per repeat unit of any of formulae (IIa), (IIb), (IIc), (IId) and/or (IIe) in its deprotected form is =0.

Such an antibiofouling polymer is termed a "polyzwitterionic" polymer.

Preferably, n is an integer selected from about 10 to about 2500, from about 30 to about 2500, from about 50 to about 2500, from about 100 to about 2500, or from about 150 to about 2500, preferably from about 250 to about 2500, for example from about 250 to about 750, from about 500 to about 1000, from about 750 to about 1250, from about 1000 to about 1500, from about 1250 to about 1700, from about 1500 to about 2000, from about 1750 to about 2250, or from about 2000 to about 2000, or from about 250 to about 1500 to about, from about 1000 to about 2500; etc., or even more preferably comprises a range formed by any of two of the above values, most preferably e.g. from about 100 to about 2500, or from about 150 to about 2500, preferably from about 250 to about 2500.

Likewise preferably, m is an integer selected from about 0 to about 20, from about 1 to about 20, from about 2 to about 20, from about 0 to about 15, from about 1 to about 15, from about 2 to about 15, most preferably from about 0 to about 10, from about 1 to about 10, from about 2 to about 10, from about 0 to about 5, from about 1 to about 5, from about 2 to about 5, from about 3 to about 5, or from about 4 to about 5, or may be selected from any of the values 0, 1, 2, 3, 4, 5, 6, 7, 8, 9, 10, 11, 12, 13, 14, 15, 16, 17, 18, 19 or 20, or even more preferably comprises a range formed by any of two of the above values.

Likewise preferably, q and r are integers independently selected from about 1 to about 10, from about 2 to about 10, from about 3 to about 10, from about 4 to about 10, from about 5 to about 10, from about 1 to about 5, from about 2 to about 5, from about 3 to about 5 or from about 4 to about 5, or may be selected from any of the values 1, 2, 3, 4, 5, 6, 7, 8, 9 or 10, or even more preferably comprise a range formed by any of two of the above values.

In the context of the inventive antibiofouling polymer, the terms "hydrophobic group" or "hydrophobic moiety" preferably refer to a "hydrophobic group" or "hydrophobic moiety" as generally defined above having a property such that an affinity of the (hydrophobic) group for water is low (e.g. being non-polar).

According to a specific aspect, the hydrophobic group of $R_9$, $R_{11}$, $R_{12}$, $R_{14}$, $R_{15}$, or $R_{16}$ of the antibiofouling polymer having as a monomeric repeat unit a structure according to any of formulae (IIa), (IIb), (IIc), (IId) and/or (IIe) may be selected from a $C_1$-$C_{12}$ or $C_1$-$C_6$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group as defined above, preferably from a linear or branched substituted or unsubstituted $C_1$-$C_{12}$ alkyl group as defined above, e.g., a linear or branched substituted or unsubstituted $C_1$-$C_{12}$ alkyl group or $C_1$-$C_6$ alkyl group.

The antibiofouling polymers of the crosslinked network structure comprising as a repeat unit a structure according to any of formulae (IIa), (IIb), (IIc), (IId) and/or (IIe), or a combination thereof, preferably exhibit a molecular weight of more than 1,000, 2,000 or 3,000 g mol$^{-1}$, of more than 10,000 g mol$^{-1}$, preferably of more than 30,000 g mol$^{-1}$, even more preferably more than 50,000 g mol$^{-1}$ or more than 75,000 g mol$^{-1}$. Advantageously, such antibiofouling and/or antibiofouling polymers of the crosslinked network exhibit a molecular weight of more than 100,000 g mol$^{-1}$, or even a molecular weight of at least 150,000 g mol$^{-1}$, a molecular weight of at least 200,000 g mol$^{-1}$, a molecular weight of at least 300,000 g mol$^{-1}$, or a molecular weight of at least 400,000 g mol$^{-1}$, a molecular weight in a range of about 10,000 g mol$^{-1}$ to about 1,000,000 g mol$^{-1}$, a molecular weight in a range of about 30,000 g mol$^{-1}$ to about 1,000,000 g mol$^{-1}$, a molecular weight in a range of about 50,000 g mol$^{-1}$ to about 1,000,000 g mol$^{-1}$, a molecular weight in a range of about 75,000 g mol$^{-1}$ to about 1,000,000 g mol$^{-1}$, a molecular weight in a range of about 10,000 g mol$^{-1}$ to about 1,000,000 g mol$^{-1}$, a molecular weight in a range of about 30,000 g mol$^{-1}$ to about 1,000,000 g mol$^{-1}$, a molecular weight in a range of about 50,000 g mol$^{-1}$ to about 1,000,000 g mol$^{-1}$, a molecular weight in a range of about 75,000 g mol$^{-1}$ to about 1,000,000 g mol$^{-1}$, a molecular weight in a range of about 100,000 g mol$^{-1}$ to about 1,000,000 g mol$^{-1}$, a molecular weight in a range of about 150,000 g mol$^{-1}$ to about 1,000,000 g mol$^{-1}$, a molecular weight in a range of about 200,000 g mol$^{-1}$ to about 1,000,000 g mol$^{-1}$, a molecular weight in a range of about 300,000 g mol$^{-1}$ to about 1,000,000 g mol$^{-1}$, a molecular weight in a range of about 400,000 g mol$^{-1}$ to about 1,000,000 g mol$^{-1}$, a molecular weight in a range of about 150,000 g mol$^{-1}$ to about 900,000 g mol$^{-1}$, a molecular weight in a range of about 200,000 g mol$^{-1}$ to about 800,000 g mol$^{-1}$, a molecular weight in a range of about 300,000 g mol$^{-1}$ to about 700,000 g mol$^{-1}$, a molecular weight in a range of about 300,000 g mol$^{-1}$ to about 700,000 g mol$^{-1}$, a molecular weight in a range of about 200,000 g mol$^{-1}$ to about 700,000 g mol$^{-1}$, a molecular weight in a range of about 150,000 g mol$^{-1}$ to about 700,000 g mol$^{-1}$, a molecular weight in a range of about 100,000 g mol$^{-1}$ to about 700,000 g mol$^{-1}$, a molecular weight in a range of about 750,000 g mol$^{-1}$ to about 700,000 g mol$^{-1}$, a molecular weight in a range of about 50,000 g mol$^{-1}$ to about 700,000 g mol$^{-1}$, a molecular weight in a range of about 30,000 g mol$^{-1}$ to about 700,000 g mol$^{-1}$, a molecular weight in a range of about 10,000 g mol$^{-1}$ to about 700,000 g mol$^{-1}$, most preferably a molecular weight in a range of about 30,000 g mol$^{-1}$ to about 1,000,000 g mol$^{-1}$, e.g. about 10,000 g mol$^{-1}$, about 30,000 g mol$^{-1}$, about 50,000 g mol$^{-1}$, about 75,000 g mol$^{-1}$, about 100,000 g mol$^{-1}$, about 150,000 g mol$^{-1}$, about 200,000 g mol$^{-1}$, about 300,000 g mol$^{-1}$, about 400,000 g mol$^{-1}$, about 500,000 g mol$^{-1}$, about 600,000 g mol$^{-1}$, about 700,000 g mol$^{-1}$, about 800,000 g mol$^{-1}$, about 900,000 g mol$^{-1}$, about 1,000,000 g mol$^{-1}$, or even more or may comprises a range formed by any of two of the above values.

As outlined above, the underlying problem is preferably solved by a substrate comprising preferably covalently attached a cross-linked network of antibiofouling polymers or by a cross-linked network of antibiofouling polymers as such, the antibiofouling polymers of the network comprising a molecular weight of more than 1,000 g mol$^{-1}$ and as a repeat unit a structure according to at least one of formulae (IIa), (IIb), (IIc), (IId) and/or (IIe), or a combination thereof, all formulae as defined herein.

Hence, the cross-linked network of antibiofouling polymers may comprise either the same antibiofouling polymers, each polymer having as a repeat unit a structure according one of formulae (IIa), (IIb), (IIc), (IId) and/or (IIe), or may comprise a combination of antibiofouling polymers different to each other each antibiofouling polymer having as a repeat unit a structure according one of formulae (IIa), (IIb), (IIc), (IId) and/or (IIe).

Alternatively or additionally, the cross-linked network of antibiofouling polymers may comprise mixed antibiofouling polymers or copolymers, each of these mixed antibiofouling polymers or copolymers having more than one, e.g. two, three or more repeat units different to each other in one mixed antibiofouling polymer, the different repeat units showing a structure according one of formulae (IIa), (IIb), (IIc), (IId) and/or (IIe). Such mixed antibiofouling polymers or copolymers may comprise either the same mixed antibiofouling polymers or different mixed antibiofouling polymers, e.g. mixed antibiofouling polymers having either identical, partially identical or different repeat units with regard to other mixed antibiofouling polymers, the repeat units showing a structure according one of formulae (IIa), (IIb), (IIc), (IId) and/or (IIe).

In the context of the present invention the antimicrobial or antibiofouling polymers of the crosslinked polymer network and in particular their repeat units according to any of formulae (Ia), (Ib), (Ic), (Id), (Ie), (If), (IIa), (IIb), (IIc), (IId) and/or (IIe) may exist in particular geometric or stereoisomeric forms. The present invention contemplates all such compounds, including exo- and endo-isomers, cis- and trans-isomers, R- and S-enantiomers, diastereomers, (D)-isomers, (L)-isomers, the racemic mixtures thereof, and other mixtures thereof, as falling within the scope of the present invention. Additional asymmetric carbon atoms may be present in a substituent such as an alkyl group. All such isomers, as well as mixtures thereof, are intended to be included in this invention.

Furthermore, it will be appreciated that the antimicrobial or antibiofouling polymers of the crosslinked polymer network and in particular their repeat units according to any of formulae (Ia), (Ib), (Ic), (Id), (Ie), (If), (IIa), (II), (IIc), (IId) and/or (IIe) may be further substituted with any number of substituents or functional moieties, if necessary. E.g. the antimicrobial and/or antibiofouling polymers or their repeat units may be modified to comprise hydrophobic and hydrophilic groups attached to the polymeric backbone such that, within a structural repeat unit, hydrophobic and/or hydrophilic groups are attached to the polymeric backbone at adjacent atoms, e.g. via ester, ether or amide linkages. Additionally or alternatively, antimicrobial polymers of the crosslinked polymer network may be modified by antibiofouling polymers and vice versa as further outlined herein.

Given the benefit of this disclosure, one of ordinary skill in the art will also appreciate that synthetic methods, as described herein, utilize a variety of protecting groups and monomers as well as polymers as defined herein, which therefore may be modified and probably also provided with such protecting groups. By the term "protecting group", as used herein, it is meant that a particular functional moiety, e.g., OH, SH, or NH$_2$, is temporarily blocked such that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. Preferably, oxygen, sulfur, nitrogen, and carbon protecting groups may be utilized for this purpose. Examples of a variety of protecting groups can be found in *Protective Groups in Organic Synthesis*, Third Ed. Greene, T. W. and Wuts, P. G., Eds., lohn Wiley & Sons, New York: 1999. Such protecting groups may comprise e.g. a tert-Butyloxycarbonyl (BOC) group, a carbobenzyloxy (Cbz) group, a p-Methoxybenzyl carbonyl (Moz or MeOZ) group, a 9-Fluorenylmethyloxycarbonyl (FMOC) group, etc Amines, which are reacted with a protection group prior to their use in the inventive synthesis method, may comprise e.g. a tert-butyl carbamate (NHBoc) (see Slugovc et al., *Macromol. Rapid Commun.* 2004, 25, 1283), etc.

The antimicrobial or antibiofouling polymers of the crosslinked polymer network and in particular their repeat units according to any of formulae (Ia), (Ib), (Ic), (Id), (Ie), (If), (IIa), (IIb), (IIc), (IId) and/or (IIe) may be prepared according to any chemical synthesis that may be suitable for a skilled person. More preferably, the present invention utilizes a novel and unique approach for preparation of the herein described antimicrobial and/or antibiofouling polymers based on a ring-opening metathesis polymerization (ROMP) platform that (i) uses a minimum number of building blocks and (ii) allows the easy and independent variation of the hydrophobic and hydrophilic residues on the respective repeat units. In this approach, hydrophilic and hydrophobic components are preferably attached to a polymerizable norbornene or oxanorbornene group, or any derivative, and can be varied independently.

Accordingly, antimicrobial and/or antibiofouling polymers, which are defined by their repeat units according to any of formulae (Ia), (Ib), (Ic), (Id), (Ie), (If), (IIa), (II), (IIc), (IId) and/or (IIe), may be obtained by using the ring-opening metathesis polymerization (ROMP) method for polymerizing these repeat units, e.g. as defined below. Preferably, such a method comprises preparation of the repeat units in a first (optional) step and polymerization of the repeat units in a second step.

According to an (optional) first step of the method for preparing antimicrobial and/or antibiofouling polymers as defined herein the monomeric units of the antimicrobial and/or antibiofouling polymers having repeat units according to any of formulae (Ia), (Ib), (Ic), (Id), (Ie), (If), (IIa), (IIb), (IIc), (IId) and/or (IIe) may be prepared. E.g., an (optional) first step of the method may be carried out by utilizing an easy and modular synthetic pathway towards preparation of such monomers, preferably via three substeps.

According to a particular example antimicrobial polymers having monomers such as in formula (If) may be prepared, wherein e.g. in a first exemplary substep, preferably furan and maleic anhydride (or adequate derivatives thereof) are mixed and undergo a Diels-Alder reaction, yielding exclusively the exo-adduct in accordance with the literature (see Mantovani et al., *J. Am. Chem. Soc.* 2005, 127, 2966). This facile exemplary substep provides a first reaction product containing a polymerizable oxanorbornene group and a cyclic anhydride that allows twofold and unsymmetrical functionalization. In an exemplary second substep the anhydride obtained by the exemplary first substep may then be ring-opened with an alcohol R—OH to introduce the desired hydrophobic moiety R, wherein residue R may be defined as indicated for any of the moieties R, $R_1$ or $R_2$, in formula (If) (or equally in any of (Ia), (Ib), (Ic), (Id), (Ie)). This exemplary substep preferably yields a "half-monomer" (monoester) or, if different alcohols R—OH are used for ring-opening, even a series of half-monomers (monoesters) with the same or different hydrophobicities. This substep is particularly suitable to adapt the hydrophobic properties of the resulting polymer as necessary. All compounds obtained in the exemplary second substep may be crystallized and purified. In an exemplary third and preferably last substep, a designated hydrophilic group as defined above may be attached to the ring-opened half monomer. This exemplary third substep is particularly suitable to adapt the hydrophilic properties of the resulting polymer as necessary. If amines are used as designated hydrophilic group in this third exemplary substep, such an amine may be provided when bound to a protecting group, e.g. as defined above, as ROMP usually does not tolerate the presence of unprotected amines due to their ligating properties. The half-monomers (monoesters) may be reacted, e.g. with the protected Boc-protected 2-amino ethanol by DCC coupling, yielding a masked amphiphilic monomer or even a series of masked amphiphilic monomers, if different alcohols R—OH were used for ring-opening. The compounds obtained in the last exemplary substep may be purified, e.g. via column chromatography, precipitation or recystallization to yield pure products.

Alternatively, exemplary second and third substeps may be interchanged to provide important key intermediates, which may be reacted to the monomers as defined according to formula (If) more efficiently. According to this alternative, the second substep, i.e. ring opening, may be carried out with a Boc protected amino alcohol. Preferably, ring opening may be carried out with a Boc-protected 2-amino ethanol, similar as shown in Scheme-2. Likewise, this alternative second substep yields a "half-monomer" (monoester) having a Boc-protected amino moiety, the amino moiety preferably representing the hydrophilic moiety as defined above. In case of monomers of the antibiofouling polymers, this half-monomer preferably represents the protected form of the zwitterion. The product of this alternative exemplary second substep may be further reacted in an alternative exemplary third substep with a further alcohol R—OH to introduce the desired hydrophobic moiety R in the alternative third substep, wherein residue R may be defined as indicated for any of the moieties R, $R_1$, or $R_2$ in formula (If). All compounds obtained in the alternative exemplary second and third substeps may be purified, e.g. via column chromatography, precipitation or recystallization to yield pure product.

According to a further specific aspect of the present invention, optional exemplary step 1 of the method for preparing the antimicrobial polymers the monomeric units of the antimicrobial and/or antibiofouling polymers according to formula (If) may be carried out as outlined below in Scheme-1 by mixing furan and maleic anhydride (or adequate derivatives thereof), e.g. in toluene, which undergo a Diels-Alder reaction, yielding exclusively the exo-adduct in accordance with the literature (Mantovani et al., *J Am. Chem. Soc.* 2005, 127, 2966). This substep 1 preferably provides compound 1 as illustrated in Scheme-1 shown in the following containing a polymerizable oxanorbornene group and a cyclic anhydride that allows twofold and unsymmetrical functionalization. The anhydride 1 is then preferably ring-opened in a substep 2 with an alcohol R—OH as defined above, preferably comprising as organic moieties a methyl (a), an ethyl (b), a propyl (c), a butyl (d) an isopentyl (e) or a hexyl (f). This substep 2 allows introducing the desired hydrophobic moiety R yielding a series of half-monomers 2, in particular 2a-f with different hydrophobicities. All compounds are crystallizable and may be purified easily. In a further substep 3, a designated cationic group is preferably attached. As ROMP usually does not tolerate the presence of unprotected amines due to their ligating properties, e.g. the desired hydrophilic group ($NH^{3+}$) may be introduced in its protected tert-butyl carbamate (NHBoc) form (Slugovc et al., *Macromol. Rapid Commun.* 2004, 25, 1283). The half-monomers 2a-f may be reacted with the Boc-protected 2-amino ethanol by DCC coupling, yielding a series of masked amphiphilic monomers 3a-f (see Scheme-1). This last substep may be subjected to purification by column chromatography or precipitation to yield pure products.

Scheme-1: Exemplary Monomer Synthesis.

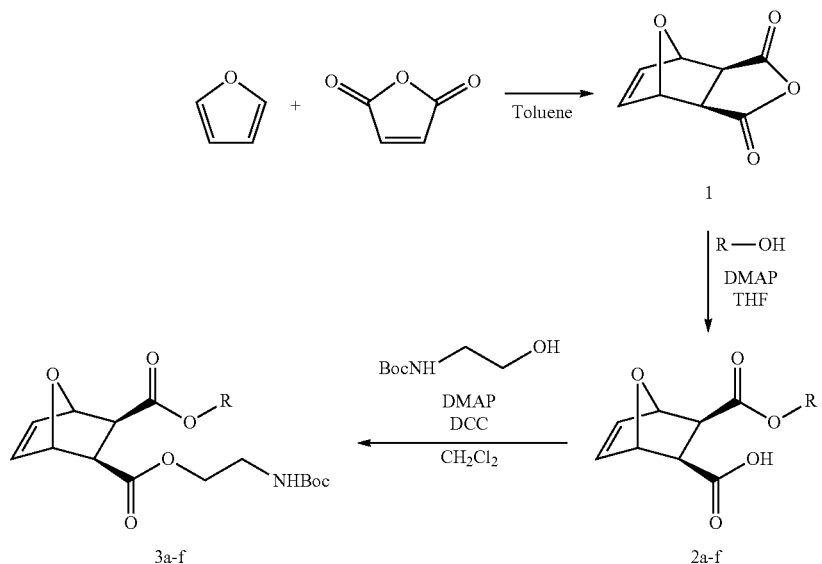

The hydrophobic component of the facially amphiphilic monomer is introduced in the second substep (R=methyl, ethyl, propyl, butyl, isopentyl or hexyl), and the protected hydrophilic moiety is attached in the last substep.

According to a particularly specific aspect, diamine monomers may be synthesized in accordance to the exemplary protocol as shown above by carrying out the ring opening metathesis in exemplary substep 2 and the reaction of the intermediate according to exemplary substep 3 with a hydrophilic component as defined above, more preferably with an amine component, by introducing e.g. the desired hydrophilic group ($NH^{3+}$) in its protected tert-butyl carbamate (NHBoc) form. This specific variant is illustrated in Scheme-2 below:

Scheme-2: Exemplary Diamine monomer synthesis.

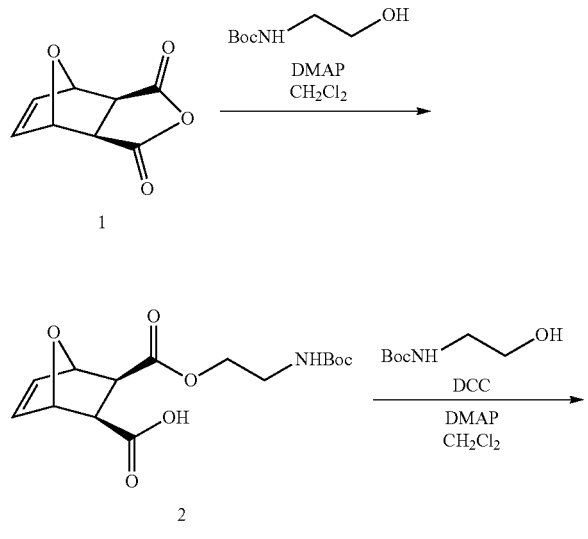

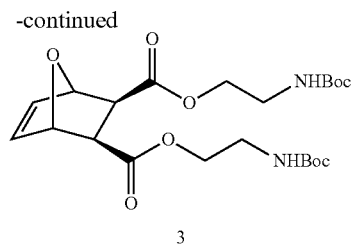

Such diamine monomers may also be used for producing co-polymers as defined herein.

The first step for preparing the monomeric subunits of formula (If) may be applied analogously to any of formulae (Ia), (Ib), (Ic), (Id) and/or (Ie) of antimicrobial polymers as defined herein and analogously to preparation of the monomeric subunits according to any of formulae (IIa), (II), (IIc), (IId) and/or (IIe) of antibiofouling polymers as defined herein. Any further method may be used to prepare antimicrobial and/or antibiofouling polymers having repeat units according to any of formulae (Ia), (Ib), (Ic), (Id), (Ie), (If), (IIa), (IIb), (IIc), (IId) and/or (IIe).

According to a second step of the method for preparing the antimicrobial and/or antibiofouling polymers the monomeric subunits according to any of formulae (Ia), (Ib), (Ic), (Id), (Ie) and/or (If) or according to any of formulae (IIa), (II), (IIc), (IId) and/or (IIe) may be subjected to a polymerization reaction. The polymerization of these monomers as obtained according to optional first step of the inventive method, preferably via substeps 1, 2 and 3 of the first step as discussed above or an analogous method, may be carried out using Grubbs catalyst, preferably the third generation Grubbs catalyst (Dichloro-di(3-bromopyridino)-N,N'-dimesitylenoimidazolino-Ru═CHPh (G3)) or a modified Grubbs catalyst G3' (Grubbs $3^{rd}$ generation catalyst with pyridine as ligands (G3') instead of the traditional G3 with 2-bromo pyridine ligands, see following formula):

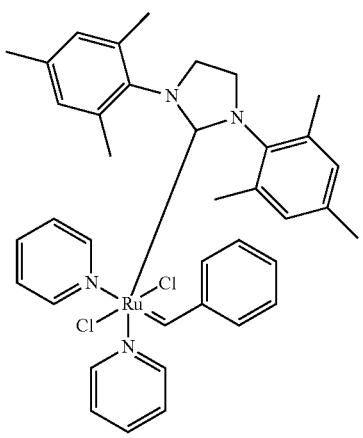

G3'

In this context, such a third generation Grubbs catalyst (G3) as well as the modified third generation Grubbs catalyst (G3') may be prepared according to the procedure outlined by Grubbs and coworkers (see Love, J. A.; Morgan, J. P.; Trnka, T. M.; Grubbs, R. H. *Angew. Chem., Int. Ed.* 2002, 41, 4035). These catalysts are preferably fully soluble in the solvents used herein. Grubbs catalyst G3 or more preferably modified Grubbs catalyst G3', is preferably (fully) solubilized in an unpolar solvent, such as dichoromethane or THF. The mixtures are then preferably subjected to at least one, two or even three freeze-thaw cycles. The polymerization is started upon mixing the monomers and the catalyst and is carried on until specific termination of the polymerization reaction. The reaction is preferably carried out between about 3 and about 60 minutes, more preferably between about 3 and 40 about minutes, even more preferably between about 20 and 40 about minutes, e.g. in a time of about 30 minutes. Gelation of the polymer is also preferably avoided. Temperatures are usually in a range of between about 15° C. and about 30° C., preferably in a range of between about 20° C. and about 25° C., e.g. about room temperature.

Instead of the third generation Grubbs catalyst (G3) or a modified third generation Grubbs catalyst (G3') other catalysts may be used which are known to a skilled person and suitably allow polymerization of monomeric subunits according to any of formulae (Ia), (Ib), (Ic), (Id), (Ie) and/or (If) or according to any of formulae (IIa), (II), (IIc), (IId) and/or (IIe) in a polymerization reaction. Such catalysts may comprise, e.g. Grubbs $1^{st}$ generation catalyst, Grubbs $2^{nd}$ generation catalyst, Grubbs-Hoveyda catalyst ($1^{st}$ or $2^{nd}$ generation), or the structurally similar catalysts from BASF, Evonik, Unicore, Zannan, ITCF, Cazan, Omega Cat Systems, most of which are available through STREM Chemicals, Postfach 1215, 77672 Kehl, (http://www.strem.com/uploads/resources/documents/ru_metathesiscat.pdf, see also e.g. STREM-catalogue "Metal Catalysts for Organic Synthesis 2012", available from abcr GmbH & Co. KG, Im Schlehert 10, 76187 Karlsruhe).

Specific termination of the polymerization reaction is typically carried out using a terminating agent. Preferably, the "living" polymer (e.g. the inventive antimicrobial and/or antibiofouling polymers with a chain-end containing a ruthenium species prior to termination of the reaction) is "end-capped" or quenched with a terminating agent and the polymerization is stopped quantitatively. Such a terminating agent may be selected from any terminating agent, which is suitable for a skilled person to terminate the polymerization reaction, e.g. from an ethyl vinyl ether or a 2-butene-1,4-diol derived terminating compound selected from a pentafluorophenylester or a pentafluorophenylether, e.g. terminating compound 1 (O1-[(Z)-4-[4-oxo-4-(2,3,4,5,6-pentafluorophenoxy)butanoyl]oxybut-2-enyl] O4-(2,3,4,5,6-pentafluorophenyl)butanedioate):

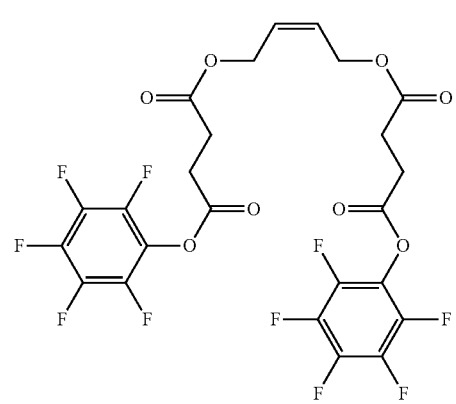

1 or terminating compound 2 ((2,3,4,5,6-pentafluorophenyl) 3-[(Z)-4-[3-oxo-3-(2,3,4,5,6-pentafluorophenoxy)propoxy]but-2-enoxy]propanoate):

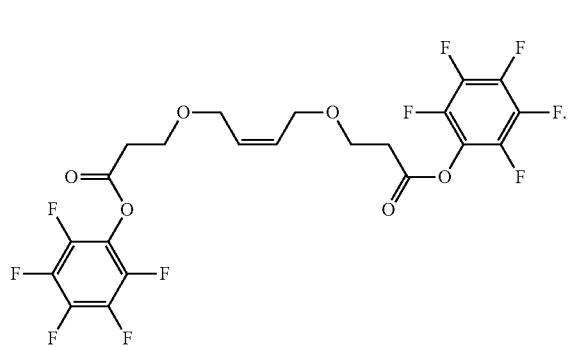

2

Such terminating agents 1 and 2 may also be used to end-functionalize the living polymers (i.e. the antimicrobial or antibiofouling polymers as defined herein during the polymerization reaction prior to termination of the reaction) in such a way as to allow reacting of the end-functionalized polymers with any further compound and/or to allow binding of the end-functionalized polymers to a surface or to a polymer as is described herein, etc. Termination of polymerization using the terminating agents 1 and 2 may be carried out as exemplarily outlined below in Scheme-3:

Scheme-3:

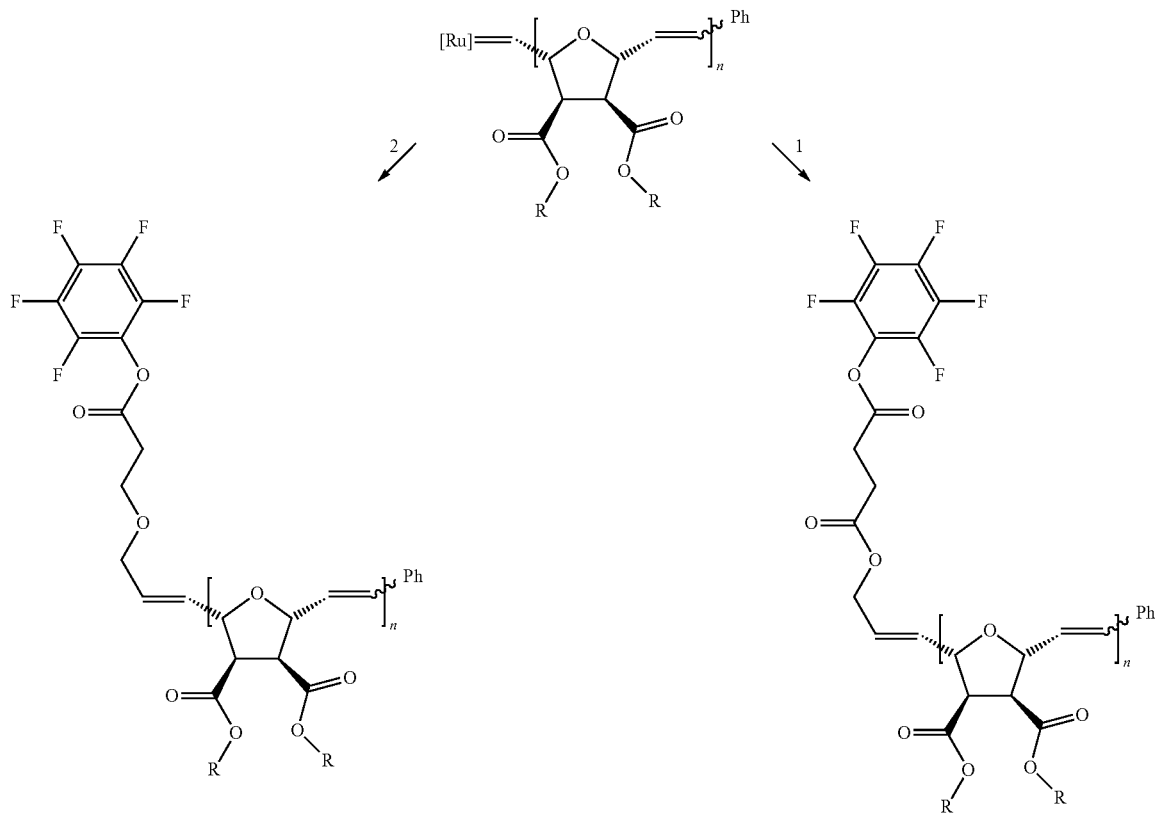

Termination of polymerization and end-functionalization of inventive living polymers with terminating agents 1 (pentafluoroallyl ester) and 2 (pentafluoroallyl ether); The shown termination reaction may be applied accordingly to antimicrobial polymers and antibiofouling polymers as defined herein. In this case the substituents R and R as shown in scheme 3 are preferably adapted according to the formulae shown above (as $R_1$, $R_2$, etc.). A is here preferably O but may be alternatively as defined above.

Termination of polymerization preferably yields precursors of the antimicrobial or antibiofouling polymers as defined herein, more precisely end-capped or end-functionalized antimicrobial and/or antibiofouling polymers as defined herein in their protected form, with molecular weights from 1,000 to 1,000,000 g mol$^{-1}$, preferably with molecular weights from 3,000 to 1,000,000 g mol$^{-1}$, more preferably with molecular weights as defined above for any of formulae (Ia), (Ib), (Ic), (Id), (Ie), (If), (IIa), (II), (IIc), (IId) and/or (IIe). Any of these end-capped or end-functionalized polymers (either protected or deprotected) are also covered by the present invention (as precursors), preferably when covalently attached in form of a crosslinked network to a surface or a substrate as defined herein. The facially amphiphilic SMAMPs having repeat units of any of formulae (Ia), (Ib), (Ic), (Id), (Ie) and/or (If) or the analogous antibiofouling polyzwitterions having repeat units of any of formulae (IIa), (IIb), (IIc), (IId) and/or (IIe) may then be obtained via polymer analogous deprotection: For this purpose, the protecting group, e.g., a Boc protecting group, is typically removed via hydrolysis, preferably with an acid, e.g. with trifluoroacetic acid or HCl, or thermally. The success of the reaction and removing of the protecting group may be controlled by NMR, if the polymers are in solution. Depending on the alkyl residue, the resulting crude polymers are water-soluble or dispersible.

According to a specific aspect of the present invention, the second step of the inventive method for preparing the inventive antimicrobial polymers having repeat units of any of formulae (Ia), (Ib), (Ic), (Id), (Ie) and/or (If) or the analogous antibiofouling polymers having repeat units of any of formulae (IIa), (II), (IIc), (IId) and/or (IIe) may be carried out as outlined below in Scheme-4. Grubbs 3$^{rd}$ generation catalyst with pyridine as ligands (G3') may be used in this reaction as a catalyst instead of the traditional G3 with 2-bromo pyridine ligands. In a typical experiment, the monomers and the respective amount of catalyst G3 or G3', preferably G3', may be dissolved in dichloromethane and subjected to three freeze-thaw cycles. Preferably, the amounts of the monomers according to any of formulae (Ia), (Ib), (Ic), (Id), (Ie) and/or (If) or according to any of formulae (IIa), (IIb), (IIc), (IId) and/or (IIe), either the single monomers or a mixture thereof, may be about 250 to about 750 g mol$^{-1}$, more preferably about 400 to about 600 g mol$^{-1}$, e.g. about 500 g mol$^{-1}$. Preferably, the amount of the catalyst may be about 0.5 mg to 2 mg e.g. 1 mg. The monomers may then be added in one shot to the vigorously stirring catalyst solution, preferably at room temperature under argon. After about 20 to about 40 about minutes, e.g. after a time of about 30 minutes, the polymer chain reaction is preferably terminated by end-capping the living polymer with an excess of a terminating agent, e.g. ethylvinyl ether (1 mL). The solution may then be allowed to stir over night. After evaporation of the solvent and drying, an aliquot of each polymer may be taken for GPC and NMR analysis. The polymerization yields the precursor polymers 4a-f (end-capped and protected). The molecular weights may be determined by GPC analysis using polystyrene standards for calibration. A specific exemplary procedure for synthesis of antimicrobial polymers as defined herein is shown in Scheme-4.

Scheme-4: Synthesis of antimicrobial polymers via ROMP.

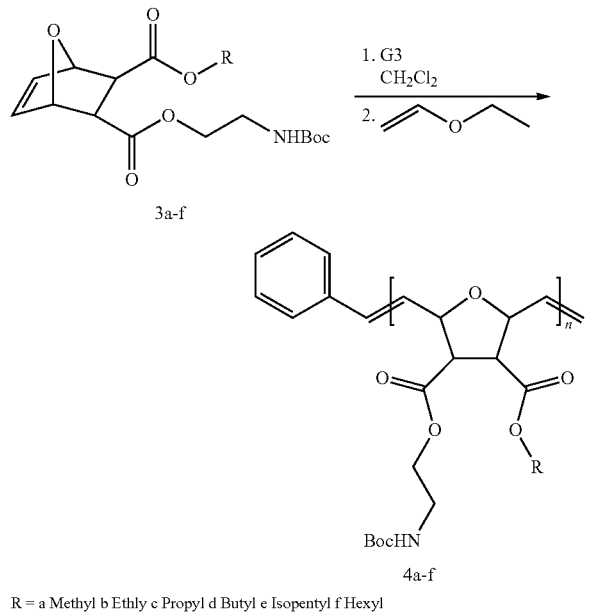

R = a Methyl b Ethly c Propyl d Butyl e Isopentyl f Hexyl

ROMP polymerization is followed by polymer analogous hydrolysis with an acid, such as trifluoroacetic acid, to yield the facially amphiphilic polymer. Likewise, this exemplary synthesis leads to the precursors of the antimicrobial polymers comprising repeat units according to any of formulae (Ia), (Ib), (Ic), (Id), (Ie) and/or (If) with molecular weights from 1,000 to 1,000,000 g mol$^{-1}$, as defined herein The antimicrobial polymers may then be obtained by deprotection subsequent to covalent binding of a crosslinked network of the antimicrobial and/or antibiofouling polymers on a surface or substrate as defined herein. Antibiofouling polymers having repeat units according to any of formulae (IIa), (IIb), (IIc), (IId) and/or (IIe) may be prepared analogously to antimicrobial polymers via ROMP using monomers having a structure according to any of formulae (IIa), (IIb), (IIc), (IId) and/or (IIe) instead of monomers having a structure according to any of formulae (Ia), (Ib), (Ic), (Id), (Ie) and/or (If).

The antimicrobial or antibiofouling polymers as defined herein may be furthermore be reacted to a crosslinked network, which is preferably covalently attached to a surface. In this context, the antimicrobial and/or antibiofouling polymers according to any of formulae (Ia), (Ib), (Ic), (Id), (Ie) and/or (If) or according to any of formulae (IIa), (IIb), (IIc), (IId) and/or (IIe) are preferably still protected, when forming the crosslinked network and preferably binding the crosslinked network covalently to the surface. In other words, the antimicrobial or antibiofouling polymers preferably carry a protecting group, more preferably a protecting group as defined herein. Hence, even though deprotection may also be carried out in solution, the present inventive approach preferably provides a surface, which has been antimicrobially coated with a crosslinked network of the protected antimicrobial and/or antibiofouling polymer or provides a crosslinked network of the protected antimicrobial and/or antibiofouling polymer. Deprotection may then be carried out subsequently to preparation of the network and optional coating the surface of a substrate with the crosslinked network of polymers by polymer analogous deprotection. Therefore, the protecting group, e.g. the Boc protecting group, is typically completely removed after formation of the crosslinked network and bonding same to the surface. Removing may occur via hydrolysis with an acid such as trifluoroacetic acid (TFA) or HCl, or thermally, etc., to obtain a covalently attached crosslinked network of the antimicrobial and/or antibiofouling polymers. Alternatively, deprotection may occur via any further method known to a skilled person, such as described e.g. in *Protective Groups in Organic Synthesis*, Third Ed. Greene, T. W. and Wuts, P. G., Eds., John Wiley & Sons, New York: 1999. Nevertheless, for the purposes of the present invention, antimicrobial and/or antibiofouling polymers as defined herein may usually include any polymer as defined herein, including such antimicrobial and/or antibiofouling polymers carrying a protection group ("precursors of the inventive antimicrobial and/or antibiofouling polymers") or being deprotected, and optionally being endcapped with a terminating agent as defined herein, unless indicated otherwise.

As defined above, the antimicrobial and/or antibiofouling polymers as defined herein may be formed to a crosslinked network and the crosslinked network may be preferably covalently attached to a surface. Alternatively and most preferably, the antimicrobial and/or antibiofouling polymers as defined herein may be provided on a surface and crosslinked to form a network as described herein preferably simultaneously to covalently attaching the network to the surface of a substrate. Such a surface may be any suitable surface, preferably any surface that can be oxidized, thiolated or silanized, preferably an inorganic surface, such as e.g. surfaces containing or comprising metals or alloys, e.g. from iron, gold, silver, copper, aluminum, nickel, chrome, titanium, molybdenum, magnesium, zirconium, etc., or ceramics, titanium or zirconium oxides (TiO$_2$, etc.), etc, or an organic or polymeric surface, such as oxidized poly(styrene) or oxidized poly(ethylene), (substituted) poly(ethyleneimine) (PEI), (substituted) poly(vinylpyridine) (PVP), (substituted) PVP-based polymers and co-polymers, poly(diallyldimethylammonium)-based, (substituted) poly(butylmethacrylate-co-amino-ethyl methyl-acrylate), (substituted) poly(2-(dimethyl-amino)-ethyl methacrylate)-based surfaces, co-polymers thereof, or any further polymer suitable for such an approach, or silicium surfaces, such as SiO$_2$, glass etc. Such surfaces may be furthermore a surface of a substrate, e.g. of any implant, dental implant, prosthesis, joint, bone, tooth, e.g. of an artificial joint, artificial bone, artificial tooth, inlay, etc., as well as any material used or to be used for implanting such a substrate, e.g. screws, anchors, any fastener or fixing material, etc. as well as any material used or to be used for implanting such a substrate. Such substrates may furthermore be selected from any medical or surgical device or tool, including implant trephine or trepan drill, scalpels, forceps, scissors, screws, fasteners and/or fixing material used for implantation, holders, clips, clamps, needles, linings, tubes, water tubes, pipes, water pipes, bottles and bottle inlays, inlays for medical equipment, etc., but also (surfaces of e.g.) operating tables, treatment chairs, catheter, stents, any wound dressing material, including plaster, gazes, bandages, but also bed sheets for clinical or medical purposes, sheets for covering medical devices, etc. Furthermore, surfaces or substrates may be selected from any further device, such as bindings or book covers, keyboards, computer keyboards, computer, laptops, displays, display covers, lamps, grips of tools and instruments, etc. Surfaces or substrates may also include any biomaterial suitable for tissue support, e.g. as a cell or tissue carrier system for wound dressing, or for volume preservation of solid body tissues. Surfaces or substrates may also include any substrate or surface used for storage of cells, tissue, organs, etc., but also any substrate or surface used for storage of food, such as refrigerators, coolers, storage boxes, etc.

For the purposes of the present invention, such a surface or (surface of a) substrate as defined herein may be pretreated to allow covalent binding of a (crosslinked) network of the (protected) antimicrobial and/or antibiofouling polymers as defined herein. More preferably, the surface as defined above may be pretreated to allow binding of a reactive compound, e.g. a reactive silane compound or a photoreactive silane compound or a thermoreactive silane compound, or a photoreactive thiol/disulfide, or a thermoreactive thiol/disulfide. Such a pretreatment may occur prior to binding a reactive compound and preferably modifies the surface to comprise, e.g., oxide or hydroxide groups, thiol moieties, etc. It thus allows binding reactive compounds by reacting with the oxide or hydroxide groups or with thiol groups on the surface. Accordingly, the surface may be treated prior to binding of a (crosslinked) network of the (protected) antimicrobial and/or antibiofouling polymers to generate e.g. hydroxide or oxide groups, e.g. with a strong base such as sodium hydroxide, ammonium hydroxide, oxygen plasma, or with UV-ozone and the like or to generate a thiol group. In the case of a metal, the metal can be subject to an oxidizing potential to generate oxide or hydroxide sites on the surface of the metal. In the case of an organic material, the organic material may be likewise pretreated to comprise e.g. oxide or hydroxide groups, etc. Alternatively, the organic material already comprises e.g. oxide or hydroxide groups, thiol moieties, etc. When binding to the surface, preferably a covalent bond forms between the surface, e.g. its oxide or hydroxide groups, and the reactive compound, e.g. a reactive silane compound or a photoreactive silane compound.

In the above context, typically two types of crosslinkers are distinguished for the purposes of the present invention. One type of crosslinkers is preferably used to attach the network of (protected) antimicrobial and/or antibiofouling polymers as defined herein to a surface. Such crosslinkers are preferably selected in the following from "photocrosslinkers" or "thermocrosslinkers". The approach will thus be termed generally "photocrosslinking approach", if photoreactive crosslinkers are used, or "thermocrosslinking approach", if thermoreactive crosslinkers are used. Suitable crosslinkers are defined below. These two approaches are preferably referred to attaching the network of antimicrobial and/or antibiofouling polymers to a (pretreated) surface. A further type of crosslinker is preferably used to form the network of (protected) antimicrobial and/or antibiofouling polymers as defined herein, either prior to or simultaneously to or even subsequently to attaching the network to a surface. Such crosslinkers may be selected from in the following e.g. from multifunctional "thiol crosslinkers", which preferably carry at least two thiol moieties. In this context, such an approach is preferably termed "Thiol-ene approach" and is preferably referred to formation of the network of antimicrobial and/or antibiofouling polymers as defined herein through addition of the multifunctional thiol crosslinkers to the double bonds ("enes").

Hence, in this context, the term "photocrosslinking approach" typically means covalently attaching the antimicrobial or antibiofouling polymers or a crosslinked network as defined herein to a (pretreated) surface as defined herein via a photoreactive compound, preferably simultaneously to forming the crosslinked network using the thiol-ene cross linking approach. For this purpose, the (pretreated) surface is preferably further functionalized.

According to a preferred aspect, a (thiol-ene)(thiol-ene) crosslinked network of the antimicrobial or antibiofouling polymer as defined herein is covalently attached to a (pretreated) surface or a substrate as defined herein via a photoreactive compound ("photocrosslinking approach") or via a thermoreactive crosslinker ("thermocrosslinking approach").

According to one aspect of such a photocrosslinking approach, the (pretreated) surface may be preferably (further) functionalized with a photoreactive compound. In this context, suitable photoreactive compounds, which may be covalently attached to such a (pretreated) surface, may comprise, without being limited thereto, e.g. any silane, thiol or disulfide compound, preferably as mentioned herein, which have at least one photoreactive group thereon and allows formation of a covalent bond, e.g. silane compounds having mono-, di-, or tri-silane moieties, preferably silane compounds having at least one tri($C_1$-$C_3$)alkoxysilyl group and at least one photoreactive group as defined herein and/or chlorosilanes. Suitable tri($C_1$-$C_3$)alkoxysilyl groups include e.g. trimethoxysilyl, triethoxysilyl, and tripropoxysilyl, chlorosilanes, and combinations thereof. More preferably, photoreactive silane compounds may comprise, e.g., triethoxysilane benzophenone, (4-benzoylbenzoyl)amino($C_1$-$C_3$)alkyltri($C_1$-$C_3$)alkoxy silane, (4-benzoylbenzoyl)aminopropyltrimethoxy silane, (4-benzoylbenzoyl) aminoethyltrimethoxy silane, and 4-(3'-chlorodimethylsilyl) propyloxybenzophenone, or the corresponding thiol, dithiol or disulfide compounds, for example the compound depicted below:

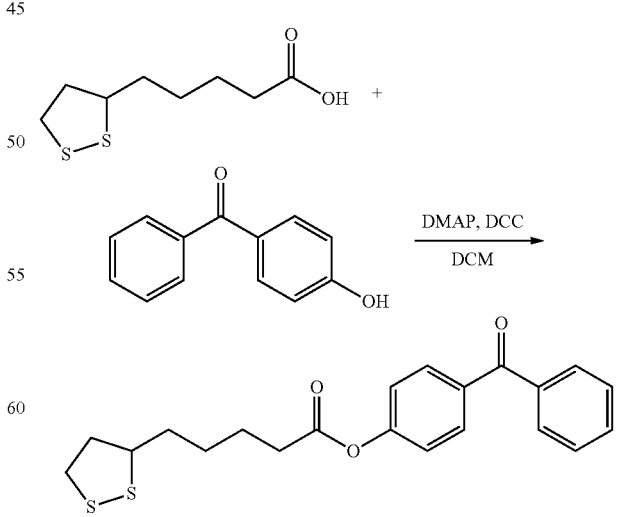

1

Thiol compounds suitable for such a photocrosslinking approach may be selected from any (photoreactive) thiol crosslinker, preferably (photoreactive) di-, tri-, tetrafunctional or multifunctional thiol crosslinker as defined herein and/or from adducts/condensation products of photoreactive compounds and thiol compounds, e.g. an condensation product between benzophenone or any and a thiol-crosslinker as defined herein.

Photoreactive compounds as defined above can be desirable because they can both bind the (pretreated) surface and then, after photoactivation, bind the (thiol-ene)-crosslinked network formed by antimicrobial or antibiofouling polymers as defined herein. Therefore, the binding procedure of binding a further compound to the surface, such as the (thiol-ene)(thiol-ene) crosslinked network formed by antimicrobial and/or antibiofouling polymers, can be simplified because only a limited number of compounds needs to be applied, each of which exhibits specific properties. Binding of the photoreactive compound to the (pretreated) surface preferably occurs via its silane moiety, if a silane compound is used, alternative via any further functionality, if a non-silane compound is used, e.g. hydroxyl moieties, COOH moieties, etc., or any further functional moiety of these crosslinkers suitable to bind to the pretreated surface. Furthermore, binding of the thiole-ene crosslinked network formed by inventive antimicrobial or antibiofouling polymers preferably occurs via the at least one photoreactive moiety of the photoreactive compound.

According to an alternative aspect of the photocrosslinking approach, the (pretreated) surface may be functionalized with a reactive silane, thiol or disulfide compound as defined herein, which does not comprise a photoreactive moiety. In this context, the reactive silane, thiol or disulfide compound is preferably covalently attached to the (pretreated) surface as defined herein in a first step. Then, preferably, a photoreactive crosslinking agent is bound to the silane, thiol or disulfide e.g. via a reactive moiety of the silane, thiol or disulfide, e.g. an SH-moiety, a hydroxyl moiety, a —COOH moiety, etc. In a final step, preferably a (thiol-ene) crosslinked network formed by the antimicrobial or antibiofouling polymer as defined herein is preferably simultaneously covalently attached to the surface via the photoreactive moiety of the photoreactive crosslinking agent in a photocrosslinking reaction, e.g. via UV activation.

In this context, a reactive silane compound, which does not comprise a photoreactive moiety and which may be covalently attached to the (pretreated) surface as defined herein in a first step, is preferably selected from silane compounds having at least one or at least two tri($C_1$-$C_3$) alkoxysilyl groups. Such silane compounds may provide a more hydrolytically stable bond to the substrate at least because each tri($C_1$-$C_3$)alkoxysilyl group can result in a bond (Si—O-Metal) with the surface. Examples of suitable tri($C_1$-$C_3$)alkoxysilyl containing silane compounds include, but are not limited to bis(trimethoxysilyl)hexane, bis(trimethyoxysilyl)ethane, and bis(trimethoxysilylethyl)benzene, preferably 1,4-bis(trimethoxysilylethyl)benzene. Furthermore, a mixture of these reactive silane compounds, preferably of tri($C_1$-$C_3$)alkoxysilyl silane compounds, can be used. The silane compound may also include [gamma]-methacryloxypropyltrimethoxysilane, either alone or in combination with other silanes, e.g. [gamma]-methacryloxypropyltrimethoxysilane and 1,4-bis(trimethoxysilylethyl)benzene. The silane compound may also have hydrophobic properties, e.g. selected from 3-(3-methoxy-4-methacryloyloxyphenyl) propyltrimethoxysilane. Additionally, the reactive silane compound may be selected from e.g. dimethyl chlorosilane, methyldichlorosilane or trichlorosilane. In the latter cases (also for all chlorosilanes), the silanization reaction is preferably carried out under exclusion of moisture in dry toluene and in the presence of a base, e.g. triethylamine.

Furthermore, a photoreactive crosslinking agent, which may be bound to the (preferably already covalently attached) reactive silane compound may be selected from any suitable photoreactive crosslinking agent known to a skilled person to be photoreactive. Furthermore, such a photoreactive crosslinking agent has preferably at least one latent photoreactive group that can become chemically reactive when exposed to an appropriate energy source, e.g. UV-radiation (UV-activation), visible light, microwaves, etc. As used herein, the phrase "photoreactive group" refers to a chemical moiety that is sufficiently stable to remain in an inactive state (i.e., ground state) under normal storage conditions but that can undergo a transformation from the inactive state to an activated state when subjected to an appropriate energy source. Photoreactive groups respond to specific applied external stimuli to undergo active species generation with resultant covalent bonding to an adjacent chemical structure, e.g., as provided by the same or a different molecule. Photoreactive groups can thus be chosen to be responsive to an appropriate energy source, e.g. UV-radiation, visible light/radiation, microwaves, etc.

Such a photoactivation typically involves addition of an appropriate energy source as defined above, e.g. UV-radiation, visible light, microwaves, etc., preferably sufficient to allow covalent binding of the photoreactive moiety to the inventive antimicrobial and/or antibiofouling polymer. Preferably, the inventive antimicrobial and/or antibiofouling polymer is bound via UV-radiation (UV-mediated crosslinking). More preferably, the integral light intensity at the sample location is typically about 50 to 150 mW $cm^{-2}$, preferably about 75 to 125 mW $cm^{-2}$, more preferably about 90 to 110 mW $cm^2$, e.g. about 100 mW $cm^2$. For UV-activation any suitable energy source may be applied known to a skilled person, e.g. a high-pressure mercury UV lamp, such as a high-pressure mercury UV lamp (e.g. 500W, preferably from Oriel), or a StrataLinker 2400 (75 W, Stratagene). UV-activation may be about 2-300 min.

Suitable photoreactive groups in the context of the present invention include, for example, azides, diazos, diazirines, ketones, and quinones. Upon "activation" with an appropriate energy source, the photoreactive group generates an active species such as free radicals including, for example, nitrenes, carbenes, and excited states of ketones.

According to one specific aspect of the photocrosslinking approach, each photoreactive group on the photoreactive crosslinking agent can abstract e.g. a hydrogen atom from an alkyl group on either the silane compounds, the hydrolysis reaction product of the silane compound, the polymeric reaction product formed from the hydrolysis reaction product of the silane compound, or a combination thereof, and/or the inventive antimicrobial or antibiofouling polymer as defined above to be covalently attached. By covalently attaching to both the silane compound and the antimicrobial or antibiofouling polymer of the crosslinked polymer network as defined herein, the photoreactive crosslinking agent promotes adhesion and/or increases binding strength when attaching the antimicrobial or antibiofouling polymer of the crosslinked polymer network to a surface as described herein.

Preferably, the photoreactive crosslinking agent is an aryl ketone, such as acetophenone, benzophenone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photoreactive crosslinking agent include quinone such as, for example anthraquinone. The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. The radical pair, or free radical, can also be used to incite chain polymerization if the appropriate monomer species are present. If a reactive bond (e.g., carbon/hydrogen) is not available for bonding, the ultraviolet light-induced excitation of the benzophenone group is reversible and the molecule returns to ground state energy level upon removal of the energy source.

Alternatively, the photoreactive crosslinking agent may be selected from e.g. arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide, or diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate; etc. R may be preferably hydrogen or an alkyl as defined above. Other photoreactive groups include the diazirines (—$CHN_2$) such as 3-trifluoromethyl-3-phenyldiazirine; and ketenes CH—C—O) such as ketene and diphenylketene.

Preferably, covalently attaching antimicrobial or antibiofouling polymer of the (thiol-ene) crosslinked polymer network as defined herein to a surface via photocrosslinking, specifically to the photoreactive group of the photoreactive crosslinking agent, usually occurs via photoactivation involving one or more photoreactive moieties of the photoreactive crosslinking agent or the photoreactive silane compound. Covalent attaching may occurs subsequently or simultaneously to formation of the (thiol-ene) crosslinked polymer network of antimicrobial or antibiofouling polymer as defined herein.

According to a further aspect the antimicrobial or antibiofouling polymers or a crosslinked network as defined herein may be covalently attached to a (pretreated) surface as defined herein via a thermoreactive compound, preferably a thermocrosslinker, following the afore mentioned "thermocrosslinking approach", preferably simultaneously to forming the crosslinked network using the thiol-ene cross linking approach. For this purpose, the (pretreated) surface is preferably further functionalized with a thermocrosslinker. In the context of the present invention, such a thermocrosslinker may be selected from any suitable compound forming covalent bonds to a substrate and/or the antimicrobial or antibiofouling polymers or a crosslinked network as defined herein upon subjecting the compound to heat treatment, e.g. $Cl(Me)_2$-Si—$CH_2$—$CH_2$—$C_6H_4$—$SO_3$—$N_3$, etc.

According to another preferred aspect, a (thiol-ene) crosslinked network of the antimicrobial or antibiofouling polymers as defined herein is preferably formed via a Thiol-crosslinker to form covalent bonds between the antimicrobial or antibiofouling polymers via their double bonds ("Thiol-ene crosslinking approach"). Such formation of the network structure can be carried out prior to attaching the polymer network of the antimicrobial or antibiofouling polymers as defined herein to a surface or simultaneously or even subsequently.

For any of these variants, the antimicrobial or antibiofouling polymers as defined herein are preferably mixed with a multifunctional crosslinker, preferably a di-, tri-, tetrafunctional or multifunctional crosslinker, preferably a multifunctional thiol crosslinker, more preferably preferably a di-, tri- or even tetrafunctional thiol crosslinker, which allows crosslinking of the antimicrobial or antibiofouling polymers as defined herein to form a crosslinked network. In this context, the term "multifunctional" preferably refers to the number of thiol-moieties or SH-moieties of such a crosslinker compound, e.g. 2, 3, 4, 5, 6, 7, 8, 9, 10 or even more thiol-moieties or SH-moieties may be contained in such a multifunctional thiol crosslinker.

Crosslinking the antimicrobial or antibiofouling polymers as defined herein with each other preferably occurs via activation of the double bonds of the repeat units of the antimicrobial or antibiofouling polymers as defined herein, e.g. thermally or via photoactivation as described above, and thereby crosslinking the polymers with each other. Generally, for this purpose, a solution of antimicrobial or antibiofouling polymers as defined herein in their protected form and a multifunctional crosslinker as defined herein, e.g. a tetrafunctional thiol cross-linker (SH), may be mixed and then spin-coated, dip-coated or spray-coated onto the surface of a substrate, or the mixture may be kept in solution. Upon activation, e.g. irradiation with UV light, the antimicrobial or antibiofouling polymer precursors are crosslinked to neighboring polymer chains of other antimicrobial or antibiofouling polymers as defined herein through the multifunctional thiol moieties. A deprotection step then yields the antimicrobial and/or antibiofouling functionality.

Alternatively, the thiol-ene crosslinking of antimicrobial or antibiofouling polymers as defined herein with each other may occur simultaneously to attaching the antimicrobial or antibiofouling polymers of the polymers as defined herein to the surface of a substrate. Generally, for this purpose, a solution of antimicrobial or antibiofouling polymers as defined herein in their protected form and a multifunctional crosslinker as defined herein, e.g. a tetrafunctional thiol cross-linker (SH), may be is spin-coated onto the surface of a substrate that has been preferably pretreated as mentioned above and modified with a photoreactive crosslinking agent, e.g. a benzophenone crosslinker (BP). Upon activation, e.g. irradiation with UV light, the antimicrobial or antibiofouling polymers as defined herein are simultaneously attached to the surface through the benzophenone cross-linker and to neighboring polymer chains of other antimicrobial and/or antibiofouling polymers as defined herein. These covalent attachments are represented in the following scheme by a dot (•) in the image below. A deprotection step then yields the antimicrobial or antibiofouling functionality.

Scheme:

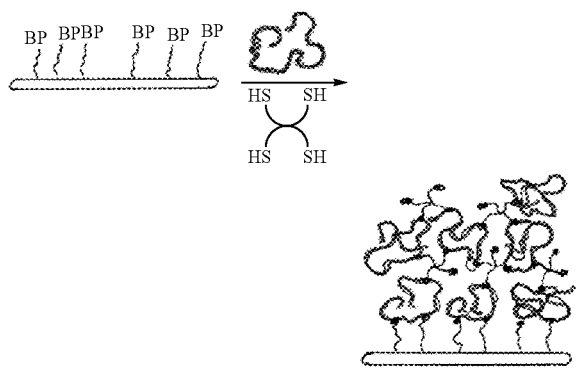

The pretreated surface exemplarily comprises benzophenone as a photocrosslinker represented by "BP". The Thiol-crosslinker is exemplarily a tetrafunctional crosslinker, wherein the Thiol-moieties are represented by "SH"

According to the present invention, a multifunctional crosslinker suitable for the "Thiol-ene crosslinking approach" may be preferably selected from a di-, tri-, tetrafunctional or multifunctional crosslinker, preferably a multifunctional thiol crosslinker, more preferably preferably a di-, tri- or even tetrafunctional thiol crosslinker, e.g. 1,2-ethandithiol, 1,3-propane trithiol, analogous higher bifunctional homologoues thereof, analogous tri- and tetrafunctional aliphatic homologoues thereof including ethane-1,1,2,2-tetrathiol, ethene-1,1,2,2-tetrathiol, and pentaerythryltetrathiol (=2,2-bis(mercaptomethyl)propane-1,3-dithiol,

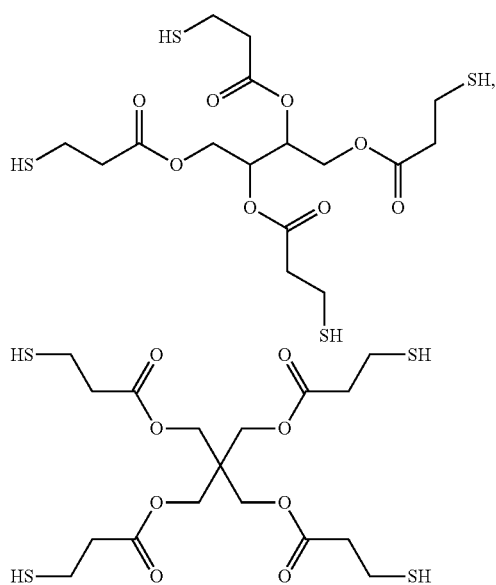

2,2'-(ethylenedioxy)diethanethiol and higher bifunctional homologoues thereof such as tetra(ethylene glycol) dithiol and hexa(ethylene glycol) dithiol, ananolgous trifunctional ethylenen glycol and polyethylen glycol thiols, and analogous ethylenen glycol and polyethylen glycol tetrafunctional thiols, 1,4-benzenedimethanethiol and analogous bi-, tri, or tetrafunctional aromatic thiols including 2,2-bis(sulfanylm- ethyl)propane-1,3-dithiol), benzene-1,2,4,5-tetrathiol, SH-functionalized nanoparticles, etc.

According to one particular preferred aspect, a crosslinked network of antimicrobial or antibiofouling polymer as defined herein is preferably attached to a surface of a substrate as defined herein simultaneously to forming the crosslinked network, preferably according to the following steps:

a) Optionally pretreating a surface of a substrate as defined herein to comprise oxide or hydroxide groups;
b) Optionally functionalizing the pretreated surface by covalently attaching a reactive silane, thiol or disulfide compound as defined herein to the pretreated surface as obtained according to step a);
c) Covalently attaching a photoreactive crosslinking agent as defined herein to a pretreated surface of a substrate preferably obtained according to step b);
d) Coating the surface of the substrate as obtained according to step c) with a mixture containing one or more (protected) antimicrobial or antibiofouling polymers as defined herein, the antimicrobial or antibiofouling polymers comprising a molecular weight of more than 1,000 g mol$^{-1}$, preferably more than 30,000 g mol-1 as defined above, and as a repeat unit a structure according to any of formulae (Ia), (Ib), (Ic), (Id), (Ie) and/or (If), or (IIa), (II), (IIc), (IId) and/or (IIe) as defined herein, and a multifunctional crosslinker as defined herein,
e) Irradiating the surface of the substrate coated with a mixture according to step d), preferably with UV light, thereby simultaneously forming a (thiol-ene) crosslinked network of the (protected) antimicrobial or antibiofouling polymers as defined herein and covalently attaching the (protected) antimicrobial or antibiofouling polymers of the crosslinked network to a photoreactive group of the photoreactive crosslinking agent;
f) Optionally repeating steps d) and e) at least once;
g) Optionally carrying out a post-irradiation treatment of the covalently attached and (thiol-ene) crosslinked network of antimicrobial or antibiofouling polymers as obtained by step e) by deprotection as defined herein, preferably via hydrolysis or thermal treatment, e.g. using an acid as defined herein, and/or by carrying out washing steps.

The steps may be carried out as generally defined herein.

According to another particular preferred aspect a crosslinked network of antimicrobial or antibiofouling polymer as defined herein is preferably attached to a surface as defined herein simultaneously to forming the crosslinked network, preferably according to the following steps:

a) Optionally pretreating a surface of a substrate as defined herein to comprise oxide or hydroxide groups;
b) Optionally functionalizing the pretreated surface by covalently attaching a photoreactive silane compound as defined herein to the pretreated surface as obtained according to step a);
c) Coating the surface of the substrate as obtained according to step b) with a mixture containing one or more (protected) antimicrobial or antibiofouling polymers as defined herein, the antimicrobial or antibiofouling polymers comprising a molecular weight of more than 1,000 g mol$^{-1}$, preferably more than 30,000 g mol-1 as defined above, and as a repeat unit a structure according to any of formulae (Ia), (Ib), (Ic), (Id), (Ie) and/or (If), or (IIa), (II), (IIc), (IId) and/or (IIe) as defined herein, and a multifunctional crosslinker as defined herein,
d) Irradiating the surface of the substrate coated with a mixture according to step c), preferably with UV light, thereby simultaneously forming a crosslinked network of the (protected) antimicrobial or antibiofouling polymers as defined herein and covalently attaching the (protected) antimicrobial or antibiofouling polymers of the crosslinked network to a photoreactive group of the photoreactive silane compound;

e) Optionally repeating steps c) and d) at least once;

f) Optionally carrying out a post-irradiation treatment of the covalently attached and crosslinked network of antimicrobial or antibiofouling polymers as obtained by step d) or e) by deprotection as defined herein, preferably via hydrolysis or thermal treatment, e.g. using an acid as defined herein, and/or by carrying out washing steps.

The steps may be carried out as generally defined herein.

Applying the different compounds as defined above to the surface as defined herein and hence coating the surface may occur using any technique known to a skilled person to apply a liquid or semi-liquid compound to a surface, e.g. via a technique, such as immersion, spraying, spray-coating, spin coating or dip coating, pouring, etc., preferably via spin-coating or dip-coating.

In this context, "spin coating" is typically a procedure used to apply uniform thin films to flat or other surfaces of a substrate, wherein an excess amount of a solution is usually placed on the surface, which is then rotated at high speed in order to spread the excess fluid by centrifugal force. Machines suitable for the inventive purpose preferably include spin coater or spinner. Typically, four distinct stages may be defined during the spin coating process: 1) Deposition of the coating fluid onto the surface of a substrate, e.g. by using a nozzle, pouring the coating solution or by spraying it onto the surface. A substantial excess of coating solution is usually applied compared to the amount that is required. 2) Acceleration of the substrate up to a final, desired, rotation speed. 3) Spinning of the substrate at a constant rate, wherein fluid viscous forces dominate the fluid thinning behavior. 4) Optionally spinning of the substrate at a constant rate, wherein solvent evaporation dominates the coating thinning behavior. In the continuous process, the steps are carried out directly after each other.

Furthermore, "dip-coating" is typically a procedure used to apply uniform thin films onto flat or cylindrical/round-shaped surfaces of substrates and typically can be separated into five stages: 1) Immersion: The substrate is preferably immersed in the solution of the coating material, either without or at a constant speed. 2) Start-up: The substrate preferably remains inside the solution for a while and is started to been pulled up. 3) Deposition: The thin layer is preferably deposited on the substrate while it is pulled up. The withdrawing is carried out by rotating at a preferably constant speed. The speed determines the thickness of the coating. 4) Drainage: Excess liquid usually drains from the surface. 5) Optionally evaporation: The solvent may evaporate from the liquid, forming the thin layer. In the continuous process, the steps are carried out directly after each other.

Preferably, the surface as defined above, preferably a pretreated and with a reactive silane (and a photoreactive crosslinker agent) functionalized surface or a pretreated and with a photoreactive silane functionalized surface, may be coated as defined above, e.g. with a mixture comprising the (protected) inventive antimicrobial or antibiofouling polymers and a multifunctional crosslinker as defined herein via spin coating or dip-coating, preferably via spin-coating.

As defined above, the thiol ene-crosslinked network formed by inventive antimicrobial or antibiofouling polymers as defined herein may be covalently attached to a surface to obtain an antimicrobially active and/or antifouling surface. Such a surface coating layer may comprise a thickness of about 10 nm to about 1000 μm, preferably a thickness from about 10 nm to about 100 μm, to about 200 μm, to about 300 μm, to about 400 μm, to about 500 μm, to about 600 μm, to about 700 μm, to about 800 μm, to about 900 μm, to about 1000 μm, to about 2000 μm, to about 3000 μm, likewise from about 100 nm, 500 nm or 1000 nm to any of the above defined upper values, etc. The thickness of the (thiol-ene) crosslinked network of antimicrobial or antibiofouling polymers as defined herein on the surface may be dependent on the different methods used for application as described herein. The thickness of the (thiol-ene) crosslinked network of antimicrobial or antibiofouling polymers as defined herein on the surface may also be dependent on the number of repetitions of the steps of coating the surface of the substrate with a mixture containing one or more (protected) antimicrobial or antibiofouling polymers as defined herein, and a multifunctional crosslinker as defined herein, and irradiating the mixture on the surface of the substrate. These steps may be repeated, e.g. 1, 2, 3, 4, or even 5 times or more. Using such a sequential approach, nearly any thickness may be obtained.

The (thiol-ene) crosslinked network formed by inventive antimicrobial or antibiofouling polymers as defined herein may comprise pores due to the crosslinked network structure. These pores are preferably formed by the intermediary space between the single polymers due to the confined geometry of the antimicrobial or antibiofouling polymers on the surface-bound network upon formation of the crosslinked network structure. In this context, it was surprisingly observed that irradiating inventive compositions/mixtures of antimicrobial or antibiofouling polymers, multifunctional cross-linkers and optionally UV active initiators lead to surfaces with defined pore sizes. These pores can be filled with further polymers containing other chemical functionalities to obtain bifunctional polymer surfaces or with any further compound, which is preferably bound to a polymer. Thus, the present inventors have found a process that allows the nano- and/or microstructuring of a surface with an antimicrobial or antibiofouling polymer in one step, with or without the need of a lithographic mask, and with tuneable pore sizes. Such pore sizes preferably may have a width of about 50-500 nm, e.g. a width of about 50 to 500 nm, of about 50 to 250 nm, of about 50 to 100 nm, of about 100 to 500 nm, of about 200 to 500 nm, of about 300 to 500 nm, etc. Crosslinked networks with such pore sizes preferably exhibit an enhanced surface area.

Due to this enhanced surface area of the herein described surface-bound crosslinked network formed by inventive antimicrobial or antibiofouling polymers, it is possible to modify them easily with further components and/or compounds, e.g. a second functional polymer component, by "grafting onto". For this purpose the further components and/or compounds are preferably end-functionalized and are reacted with the crosslinked network formed by inventive antimicrobial or antibiofouling polymers. As an example, the antimicrobial crosslinked polymer network as defined herein is preferably reacted with antibiofouling polymers as defined herein preferably carrying end-functionalized moieties as also defined herein. Alternatively, the antibiofouling crosslinked polymer network as defined herein is preferably reacted with antimicrobial polymers as defined herein preferably carrying end-functionalized moieties as also defined herein. Thus, surface-bound crosslinked networks are created that bear different functionalities with antimicrobial and/or antibiofouling activities, or even with further functionalities, such as antifungal activities, etc., if corresponding components and/or compounds are to be attached.

Accordingly, following one aspect of the present invention, components and/or compounds may be added to the crosslinked polymer network as defined herein. Such components and/or compounds may be e.g. antimicrobial and/or antibiofouling polymers as defined herein, the antimicrobial and/or antibiofouling polymers comprising a molecular weight of more than 1,000 g mol$^{-1}$, preferably more than 30,000 g mol-1 as defined above, and as a repeat unit a structure according to any of formulae (Ia), (Ib), (Ic), (Id), (Ie) and/or (If), or (IIa), (II), (IIc), (IId) and/or (IIe) as defined herein. Such further antimicrobial and/or antibiofouling polymers may either comprise the same or different structures, molecular weights, etc. Such further components and/or compounds may also comprise any other suitable polymer, such as polyacrylates, polymethacrylates, copolymers of acrylates and methacrylates, polystyrols, poly(ethylene glycol) (PEG), poly(phosphorylcholines) poly(sulfobetaines), poly(carboxybetaines), poly(oxazolins) and poly (saccharides), Chitosan, poly(dimethysiloxane), (substituted) poly(ethyleneimine) (PEI) and poly(vinylpyridine) (PVP), poly(diallyldimethylammonium), poly(butylmethacrylate-co-amino-ethyl methyl-acrylate), poly(2-(dimethyl-amino)-ethyl methacrylate), etc., wherein each polymer is preferably modified to comprise a end-functionalized moiety, preferably as defined herein, more preferably an active ester, e.g. obtained is a radical, anionic or cationic polymerisation.

Such components and/or compounds, which may be added to the crosslinked network structure may be preferably added via techniques such as "grafting onto" to the crosslinked network structure as described herein.

For the purpose of adding such components and/or compounds via "grafting onto", the polymers of the crosslinked network may be reacted with end-functionalized components and/or compounds as defined above, e.g. end-functionalized polymers as described above, preferably end-functionalized polymers comprising a molecular weight of more than 1,000 g mol$^{-1}$, preferably more than 30,000 g mol-1 as defined above, and as a repeat unit a structure according to any of formulae (Ia), (Ib), (Ic), (Id), (Ie) and/or (If), or (IIa), (IIb), (IIc), (IId) and/or (IIe) as defined herein. Such end-functionalized polymers may be obtained, e.g. in case of polymers according to any of formulae (Ia), (Ib), (Ic), (Id), (Ie) and/or (If), or (IIa), (IIb), (IIc), (IId) and/or (IIe), by reaction the (unmodified) living polymers with a terminating agent, preferably with a terminating agent as defined herein, more preferably with any of terminating agents 1 or 2 as defined before. For this purpose, the polymerization of the living polymer may be terminated as defined above at a desire point of time with these termination agents. More preferably, the polymerization of the living polymer as defined above may be terminated by termination agent 2 as defined above. Any other end-functionalized polymer as described above may be obtained analogously by terminating the polymerization reaction of such a polymer. This reaction product, i.e. an end-functionalized (protected) polymer as defined according to the present invention, may then be reacted with the polymers of the crosslinked network as defined above.

According to a further aspect of the present invention, the present invention also provides micro- and nano-structured surfaces, wherein such micro- and nano-structured surfaces are preferably formed on at least a part of a substrate as defined herein. These micro- and nano-structured surfaces preferably comprise covalently attached to at least a part of the surface of the substrate a crosslinked network of antimicrobial or antibiofouling polymers according to a predefined pattern. Such crosslinked networks of antimicrobial or antibiofouling polymers are preferably as defined above and comprise a molecular weight of more than 1,000 g mol$^{-1}$, preferably more than 30,000 g mol-1 as defined above, and as a repeat unit a structure according to any of formulae (Ia), (Ib), (Ic), (Id), (Ie) and/or (If), or (IIa), (II), (IIc), (IId) and/or (IIe). Preferably, the micro- and nano-structured surfaces are formed during formation of the crosslinked network on at least a part of the surface of the substrate.

Techniques for micro- and nano-structuring of the crosslinked network suitable for the inventive purpose may be selected, e.g. from photo-lithographic or optical lithographic methods, preferably by using photomasks or patterns with predefined structures, or by laser-based methods, either 2D- or 3D-laser methods, such as two-photon-lithography, wherein two laser beams are moved across the polymer film in such a way that enough energy for photocrosslinking is available at the crossing-point of these lasers.

For the purpose of the present invention the term "photolithography" or "optical lithography" is preferably understood as a process used in micro- or nano-structuring to selectively add layers, e.g. layer by layer, or films, preferably film by film, on at least one part of a substrate as defined herein in nano- or micro-scale and thus to enable deposition of a new material in a desired pattern upon a substrate as defined herein. The patterning thus may be applied onto a surface in one or more preferably independent and preferably consecutive steps by using either the same or different patterns or photomasks, preferably timely staggered, which allows preparing micro- or nano-architectures of a crosslinked network of the antimicrobial and/or antibiofouling polymers as herein defined as a 3D structure. Accordingly, the photolithography or "optical lithography" may be carried out in several steps, preferably to obtain 3D structures by preparing each layer according to a predetermined patterning.

Preferably, according to a specific aspect, a pattern may be applied in a first step following the general procedures as defined above for preparing antimicrobial or antibiofouling polymers as defined herein. Then, in a second step, at least one further pattern may be applied with a antimicrobial or antibiofouling polymer as defined herein, wherein this further pattern may be the same or different and wherein the antimicrobial or antibiofouling polymer may be the same or different to the afore applied antimicrobial or antibiofouling polymer, preferably the antimicrobial or antibiofouling polymers as applied in the step directly before. Following this approach, a predefined pattern of antimicrobial or antibiofouling polymers as defined herein may be obtained, wherein the predefined pattern may comprise at different parts of the pattern the same or a different thickness, preferably due to the same or a different number of layers of antimicrobial or antibiofouling polymers as defined herein, and/or the same or a different antimicrobial or antibiofouling polymer as defined herein.

The patterning, which may be applied to a surface following the above approach may be of any kind. As an example, the surface of a substrate as defined herein may be pretreated as described above and then coated with a mixture as defined before containing one or more (protected) antimicrobial or antibiofouling polymers of any of formulae (Ia), (Ib), (Ic), (Id), (Ie) and/or (If), or (IIa), (II), (IIc), (IId) and/or (IIe) as defined herein and a multifunctional crosslinker as defined herein on the entire surface of a substrate, wherein only a part of the surface is subjected to photoactivation due to a photomask or pattern. Then, only a part of the surface will be covalently attached to a crosslinked network of antimicrobial or antibiofouling polymers formed by polymers having repeat units of any of formulae (Ia), (Ib), (Ic), (Id), (Ie) and/or (If), or (IIa), (II), (IIc), (IId) and/or (IIe) as defined herein. Then, according to a second or further steps, the treatment may be repeated with either the same or a different photomaskpattern, with the same or different polymers and/or with the same or different crosslinkers. This may lead to differently formed crosslinked network structures and a simply adjustable 3D nano- or microstructuring of crosslinked networks of the polymers as described herein on the surface of a substrate.

A further method, which may be used to prepare micro- or nano-architectures of a crosslinked network of the antimicrobial or antibiofouling polymers as herein defined may comprises maskless techniques, including but not limited to laser-interference lithography or two-photon-lithography. In this context, two-photon-lithography is preferably to be understood as a direct "laser writing" technology as exemplified by the "Nanoscribe" technology (see e.g. www.nanoscribe.de or Nanoscribe GmbH, Karlsruhe, Germany). In direct laser writing, very short laser impulses (on the femtosecond scale) are used. The energy of a single photon is below the absorption limit of the photoresist. Consequently, the photoresist, in this case the inventive antimicrobial or antibiofouling polymers that have been mixed with the above described thiol-based crosslinkers, is transparent for the laser light. By focusing the laser pulse onto a nano- or microscale focal volume, there is a probability that the resist absorbs two or more photons at the same time. This allows cross linking of the inventive antimicrobial and/or antibiofouling polymers as described herein. After irradiation, a washing step may be carried out, which allows the removal of then non-crosslinked material. Thus, the desired nano- and microstructures are generated. In contrast to other maskless techniques, this allows the writing of arbitrary 3D-structures at high resolutions.

Laser interference lithography is in this context preferably understood as a setup that generates an interference pattern between two coherent laser waves, which then hits a photoresist, in this case the inventive antimicrobial and/or antibiofouling polymers that have been mixed with the thiol crosslinker. The interference pattern is a series of minima and maxima that, after a washing step, yields lines on the substrate, with a resolution limit of half the wavelength of the laser light used. With this techniques, periodical patterns that result from the overlay of interference patterns may be achieved.

According to one further embodiment the present invention also provides blended antimicrobial or antibiofouling polymers. As surprisingly found by the present inventors, the herein defined antimicrobial or antibiofouling polymers can be blended and photo-crosslinked with other polymers. This represents an important step towards the fabrication of antimicrobially active thermoplastic materials and other antimicrobially active polymer materials, as polymers usually tend to demix upon blending. The demixing of such polymer blends is prevented by covalent cross-linking the two polymers in such a mix. Hence, the present invention provides antimicrobial or antibiofouling polymers as described herein blended with at least one further polymer. For this purpose, the mix preferably comprises antimicrobial or antibiofouling polymers as defined herein comprising a molecular weight of more than 1,000 g mol$^{-1}$, preferably more than 30,000 g mol-1 as defined above, and as a repeat unit a structure according to any of formulae (Ia), (Ib), (Ic), (Id), (Ie) and/or (If), or (IIa), (IIb), (IIc), (IId) and/or (IIe), and at least one further polymer. The at least one further polymer may be selected from a further antimicrobial or antibiofouling polymers as defined herein comprising a molecular weight of more than 1,000 g mol$^{-1}$, preferably more than 30,000 g mol-1 as defined above, and as a repeat unit a structure according to any of formulae (Ia), (Ib), (Ic), (Id), (Ie) and/or (If), or (IIa), (II), (IIc), (IId) and/or (IIe), preferably different to the base polymer. More preferably, the at least one further polymer is selected from a thermoplastic polymer, poly(ethyleneimine) (PEI), substituted poly (ethyleneimine) (PEI), poly(vinylpyridine) (PVP), poly(diallyldimethylammonium)-based, poly(butylmethacrylate-co-amino-ethyl methyl-acrylate) as well as poly(2-(dimethyl-amino)-ethyl methacrylate)-based polymers, polyacrylates, polymethacrylates, copolymers of acrylates and methacrylates, polystyrols, poly(ethylene glycol) (PEG), poly(phosphorylcholines) poly(sulfobetaines), poly (carboxybetaines), poly(oxazolins) and poly(saccharides), Chitosan, poly(dimethysiloxane), etc. The mix also preferably comprises a photoreactive crosslinker, e.g. as defined herein, or any other suitable crosslinker, preferably as defined herein. Even more preferably, the at least one further polymer, preferably a thermoplastic polymer, more preferably a polymer as defined before, comprises an UV-reactive crosslinker or a corresponding moiety, e.g. as defined above for photocrosslinkers, or a thermoreactive reactive crosslinker or a corresponding moiety, e.g the thermo crosslinker styrene sulfonic acid azide. Particularly preferred in this context are e.g. benzophenon, anthracen, and further UV-crosslinking moieties. Blending of inventive antimicrobial or antibiofouling polymers as defined herein and of further polymers as defined before can be carried out by preparing a mix as described before and irradiating the mix, e.g. with UV-light, or subjecting the mix to a heat treatment, to crosslink the polymer strands of the mix.

According to a further embodiment of the present invention antimicrobial or antibiofouling polymers with pre-defined break points (R) are provided, and accordingly also crosslinked networks of such antimicrobial or antibiofouling polymers with predefined break points (R) and also surfaces to which such antimicrobial or antibiofouling polymers with predefined break points have been preferably covalently attached. These antimicrobial or antibiofouling polymers preferably comprise repeat units according to any of formulae (Ia), (Ib), (Ic), (Id), (Ie) or (If), or (IIa), (II), (IIc), (IId) and/or (IIe) as defined herein and additionally comprises breakpoints (R) as defined below. Such break points (R) are preferably located between at least two of the repeat units. Such antimicrobial or antibiofouling polymers used herein could be prepared following the methods as described above, e.g. as a block polymer. Insertion of break points then occurs preferably following the scheme below. Two general schemes of the concept for preparation such antimicrobial or antibiofouling polymers with predefined break points are outlined below:

General Scheme I:

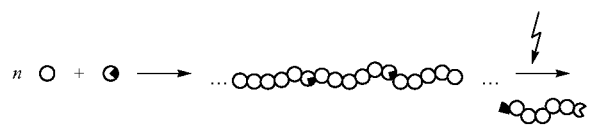

Polymerization approach towards polymers with intended break points: n equivalents of antimicrobial or antibiofouling repeat units as defined herein or polymers thereof ("monomer" 1) are copolymerized with one equivalent of (co)monomer ("monomer" 2) containing the intended break point (R) (shown as a darker circle). As a result, a polymer with an intended break point (R) per (n+1) repeat units is formed. An external stimulus then triggers the polymer degradation, so that small highly active antimicrobial fragments with n repeat units are formed. The two kinds of monomer as described here may be either copolymerized simultaneously, or may be added sequentially, such that small polymer blocks are formed.

crobial or antibiofouling polymer as defined herein. Such a block has preferably a molecular weight as defined above for the antimicrobial or antibiofouling polymers. B is then preferably a compound or a moiety which contains the predefined break point (R), which is preferably any functional group (typically located in the main chain of the polymer) that can be cleaved chemically, thermally, by radiation or otherwise. Such break point is preferably a compound or functional group selected from an ester, amide, carbonate, thiocarbonate, thiocarbamate, carbamate, or acetal, or any other compound or functional group known or suitable for a skilled person.

General scheme II:

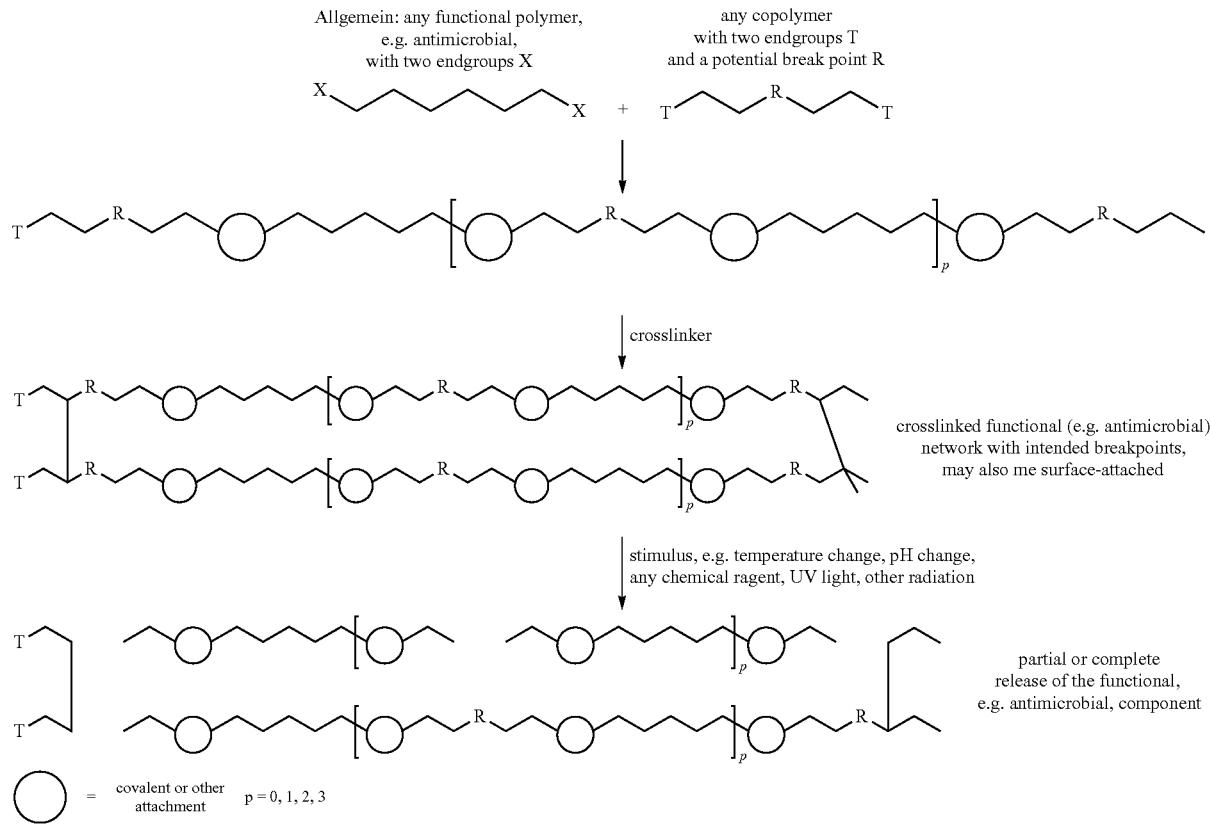

Following the above general scheme I, preferably two components, "monomers" 1 and 2, are used to prepare antimicrobial or antibiofouling polymers with predefined break points (R) according to the invention.

In general, "monomer" 1 may be a monomer having a structure as defined according to any of repeat units of formulae (Ia), (Ib), (Ic), (Id), (Ie) or (If), or (IIa), (II), (IIc), (IId) and/or (IIe) as defined herein (or may be any antimicrobial or antibiofouling polymer as defined herein preferably comprising as a repeat unit a structure according to any of formulae (Ia), (Ib), (Ic), (Id), (Ie) or (If), or (IIa), (IIb), (IIc), (IId) and/or (IIe) as defined herein). This "monomer" 1 is copolymerized with "monomer" 2 as defined below. "Monomers" 1 and 2 may either be polymerized simultaneously (to obtain a statistical copolymer) or sequentially (to obtain an ABA block or (AB)$_n$ multiblock copolymer), wherein A is preferably a (short) block of either an antimi- Following general scheme II, preferably two components, components 1 and 2, are used to prepare antimicrobial or antibiofouling polymers with predefined break points (R) according to the invention.

In general, component 1 may be any antimicrobial or antibiofouling polymer as defined herein preferably antimicrobial or antibiofouling polymers comprising a repeat unit according to any of formulae (Ia), (Ib), (Ic), (Id), (Ie) or (If), or (IIa), (IIb), (IIc), (IId) and/or (IIe) as defined herein, which is preferably prepared as described before and is end-functionalized such that it carries two reactive endgroups. End-functionalization is preferably carried out as shown above using terminating agents or reactive endgroups as defined herein. Alternatively, component 1 may be synthesized as an ABA block copolymer or an AB random polymer, wherein B is preferably a (short) block of either an antimicrobial or antibiofouling polymer as defined herein.

Such a block has preferably a molecular weight as defined above for the antimicrobial or antibiofouling polymers. A is then preferably a compound or a moiety which contains one or more reactive groups such as active esters, more preferably succinimido esters, pentafluorophenyl esters, vinyl esters, cyanomethyl esters, 4-nitropenyl esters, S-phenyl thioesters, piperidino esters, pyridyl esters, trichlorophenyl esters, phthalimido esters, pentachlorophenyl esters or 4-oxo-3,4-dihydrobenzotriazin-3-yl-ester or any other acid derivative able to react with an OH, SH or amino group on B to form an ester, thioester, carbonate, carbamate, thiocarbamate or amide bond. Alternatively, the reactive group on A may be an azide group that is able to react with a triple bond on B, etc.

Furthermore, component 2 may be any polymer or copolymer, e.g. as defined herein, wherein the polymer is preferably end-functionalized such that it carries two reactive endgroups and additionally contains an intended break point (R). Alternatively, component 2 can be synthesized as an A'B'A' block copolymer or an A'B' random, wherein B' is a polymer as defined above which additionally contains a predetermined break point (R) and A' contains one or more reactive end groups. The reactive end groups are preferably selected from a compound or functional group selected from $NH_2$, SH or OH, or a triple bond. The predefined break point (R) is preferably any compound or functional group (typically located in the main chain of the polymer) that can be cleaved chemically, thermally, by radiation or otherwise. Such break point (R) is preferably a compound or functional group selected from an ester, amide, carbonate, thiocarbonate, thiocarbamate, carbamate, acetal, etc.

The end-groups of component 1 and component 2 are preferably chosen in such a way that they form a covalent or non-covalent bond with each other, resulting in a high molecular weight polymer comprising small blocks of the antimicrobial and/or antibiofouling component and segments containing the intended break point (R).

Formation of a polymer then takes place by reacting components 1 and 2 via their reactive end groups with each other to form a covalent bond, e.g an active ester or otherwise activated acid group with OH, $NH_2$ or SH, or azide with a triple bond, respectively.

By adding a suitable bi- or multifunctional (reactive) thiol crosslinker to the resulting polymer with predefined break points (R) as defined in the general schemes I and II above, a (thiol-ene) crosslinked polymer network with intended break points (R) may be formed according to the methods set out above in general. Alternatively or additionally, such a (thiol-ene) crosslinked polymer network may be covalently attached to a surface, likewise similar as shown above for inventive (thiol-ene) crosslinked polymer networks. Crosslinkers as used for this purpose are preferably also as described above.

According to a further variant, such a polymer with predefined break points (R) may be covalently attached on a surface, as a monolayer, e.g. as described in example 1, preferably via grafting onto methods as described herein without crosslinking the polymer and without forming a network as described herein.

Advantageously, such antimicrobial or antibiofouling polymers with predefined break points (R) and polymer networks formed thereby can be fragmented at a later point of time into smaller subunits by cutting the polymer at the predefined break points (R) using an external stimulus. As already describe before, such polymers are then preferably either present in a crosslinked polymer network or as a surface-attached crosslinked polymer network or as a monolayer of polymers, preferably attached on a surface as described herein using the grafting onto method described above at a surface of a substrate.

When fragmenting such polymers with predefined break points (R), preferably small blocks of highly active antimicrobial or antibiofouling components/fragments are formed, which are then released and may act as free antimicrobial or antibiofouling compounds.

As a further alternative to the described process for preparing antimicrobial or antibiofouling polymers with predefined breakpoints (R), such a polymer, preferably comprising as a sequence:

(antimicrobially active polymer-polymer segment with intended break point $(R))_n$ or component 1-component 2-component1;

can also be obtained by any polymerization technique (in particular living/controlled anionic, cationic or radical polymerization or ring-opening polymerization) that allows the synthesis of C-D-C-D- . . . type multiblock copolymers, where C is preferably a short block of the antimicrobially active polymer, preferably as defined herein (or a antibiofouling polymer as defined herein) and D contains an intended break point (R) in the polymer main chain. The further steps are then preferably identical to the process illustrated above and depicted in the Scheme.

For the antimicrobial and/or antibiofouling polymers as described herein, such a preparation may be carried out by living ring-opening metathesis polymerization (ROMP). For this purpose, the protected antimicrobial or antibiofouling monomer is preferably first reacted with a suitable metathesis catalyst to form a short block of antimicrobial and/or antibiofouling polymer (e.g. with a molecular weight of 3000 g mol$^{-1}$) generally as described above. The living chain end of this block polymer is then preferably reacted with a co-monomer that carries the intended break point (R). This co-monomer may either be able to form a short block, or may not. In this context it is to be noted that some ROMP monomers may not react with themselves. Then, a single repeat unit carrying the intended break point (R) would be incorporated. Suitable exemplary co-monomers that introduce either ether, ester, carbonate, amide or ketal groups, or the respective thio- or nitrogen equivalents, into the main chain, are shown below:

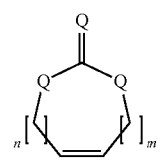

Q=O, S, NH
m, n=0, 1, 2, 3 . . .

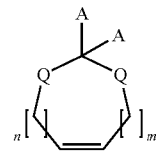

A=H, any aliphatic group, any aromatic group . . . .

Such a sequence may then repeated n times to obtain an $(AB)_n$ block copolymer. Alternatively, the two monomers may be polymerized simultaneously to yield an AB random copolymer.

Having prepared such antimicrobial and/or antibiofouling polymers via ROMP and inserting predefined break points (R) the antimicrobial and/or antibiofouling polymers with predefined break points (R) may be further utilized as described above to prepare crosslinked network structures of antimicrobial and/or antibiofouling polymers according to methods outlined above and preferably attaching such polymers to a surface of a substrate as described above. The antimicrobial and/or antibiofouling polymers with predefined break points (R) may be also utilized as indicated before to attach the (non-crosslinked) antimicrobial and/or antibiofouling polymers with predefined break points (R) to a surface of a substrate as a monolayer. In any case attachment on a surface is carried out, either as a monolayer or in form of a crosslinked network, the polymers may be released from the surface upon an external trigger, if deemed necessary.

As defined above, the crosslinked network formed by inventive antimicrobial or antibiofouling polymers as defined herein may be covalently attached to a surface or substrate as defined above, to obtain a surface or substrate comprising covalently attached to the surface of the substrate a crosslinked network of antimicrobial or antibiofouling polymers, the antimicrobial or antibiofouling polymers comprising a molecular weight of more than 1,000 g mol$^{-1}$, preferably more than 30,000 g mol-1 as defined above, and as a repeat unit a structure according to any of formulae (Ia), (Ib), (Ic), (Id), (Ie) and/or (If), or (IIa), (IIb), (IIc), (IId) and/or (IIe), as defined herein. Accordingly, as a further embodiment, the present invention also provides the use of these antimicrobial or antibiofouling polymers comprising a molecular weight of more than 1,000 g mol$^{-1}$, preferably more than 30,000 g mol-1 as defined above, and as a repeat unit a structure according to any of formulae (Ia), (Ib), (Ic), (Id), (Ie) and/or (If), or (IIa), (IIb), (IIc), (IId) and/or (IIe), for forming a crosslinked network covalently attached to the surface of the substrate, and thus coating the surface with an antimicrobial or antibiofouling polymer layer. Such a crosslinked network may be further modified as outlined above.

According to further preferred embodiment, the present invention also provides the use of a crosslinked network of antimicrobial or antibiofouling polymers, the antimicrobial or antibiofouling polymers comprising a molecular weight of more than 1,000 g mol$^{-1}$, preferably more than 30,000 g mol-1 as defined above, and as a repeat unit a structure according to any of formulae (Ia), (Ib), (Ic), (Id), (Ie) and/or (If), or (IIa), (IIb), (IIc), (IId) and/or (IIe) for providing an antimicrobial or antibiofouling coating on a surface or substrate as defined herein by covalently attaching the crosslinked network of (protected or deprotected) the antimicrobial or antibiofouling polymers to the surface or substrate as defined herein, preferably via photoactivation.

According to a final preferred embodiment, the present invention also provides the use of such a substrate or surface or the use of such a crosslinked network of antimicrobial or antibiofouling polymer for preventing microbial growth and/or biofouling. Particularly preferred the present invention provides the use such a substrate or surface for inhibiting the growth of bacteria and other pathogens, thereby preferably exhibiting a low toxicity to human cells. In this context, the covalently attached crosslinked network of antimicrobial or antibiofouling polymers preferably show significant growth reduction of bacterial pathogens on a surface of at least about 7%, preferably at least about 70%, more preferably at least about 80%, even more preferably at least about 90%, likewise even more preferably at least about 95, 96, 97, 98, 99 or 99.99%, preferably of *S. aureus* and *E. faecalis* and other pathogens

FIGURES

The FIGURES shown in the following are merely illustrative and shall describe the present invention in a further way. These FIGURES shall not be construed to limit the present invention thereto.

FIG. 1: shows micrographs of the lithographically structured film as prepared according to Example 4.

Figure 2:
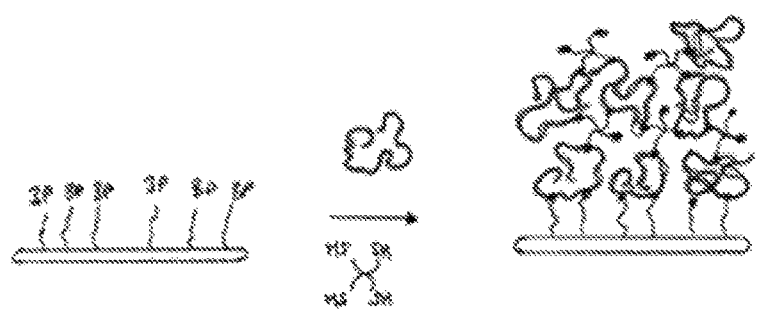

FIG. 2: shows an exemplary pretreated surface which includes benzophenone as a photocrosslinker, and an exemplary thiol-crosslinker as a tetrafunctional crosslinker, according to one embodiment.

Figure 3:
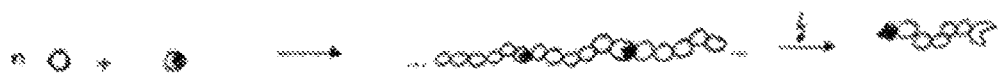

FIG. 3: shows a general scheme I of a concept for the preparation of antimicrobial or antibiofouling polymers, according to one embodiment.

EXAMPLES

The examples shown in the following are merely illustrative and shall describe the present invention in a further way. These examples shall not be construed to limit the present invention thereto.

General:

All chemicals were obtained as reagent grade from Aldrich, Fluka or Acros and used as received. HPLC grade solvents were purchased from Aldrich or Acros and used as received. THF (HPLC grade, Fisher Scientific) was distilled from sodium/benzophenone under nitrogen. Dichloromethane (HPLC grade, Fisher Scientific) was distilled from CaH$_2$ under nitrogen. Gel permeation chromatography (DMF/0.01 M LiCl, calibrated with polystyrene standards) was measured on a PSS GRAM column (PSS, Mainz, Germany). NMR spectra were recorded on a Bruker 250 MHz spectrometer (Bruker, Madison, Wis., USA).

Synthesis of a Variation of Grubbs 3$^{rd}$ Generation Catalyst:

A variation of Grubbs 3$^{rd}$ generation catalyst (original Grubbs 3$^{rd}$ generation catalyst=Dichloro-di(3-bromopyridino)-N,N'-Dimesitylenoimidazolino-Ru=CHPh; G3) was specifically synthesized similar as described previously by Grubbs and colleagues (see J. A. Love, J. P. Morgan, T. M. Trnka, R. H. Grubbs, Angewandte Chemie International Edition 2002, 41, 4035-4037). For this variation of Grubbs 3rd generation catalyst pyridine was taken instead of 3-bromo pyridine to yield the corresponding catalyst with two pyridine ligands.

Silanization of a Silicon Wafer as Substrate for Polymer Immobilization:

The crosslinking agent 4-(3-triethoxysilyl)propoxybenzophenone (=3EBP-silane) was synthesized as described in the literature (Gianelli et al., Soft Matter 2008, 4, 1443). A solution of 3EBP-silane (20 mg mL$^{-1}$ in toluene) was spin coated on a (525±25) μm thick one-side-polished 100 mm standard Si (CZ) wafer ([100] orientation, 1000 rpm, 120 s). The wafer was cured for 30 min at 100° C. on a preheated hot plate, washed with toluene and dried under a continuous nitrogen flow.

Example 1

Surface-Bound Antibiofouling Polymer (Monolayer)

1.1—Monomer Synthesis:

The monomer was obtained from exo-7-oxabicyclo[2.2.1]hept-5-ene-2,3-dicarboxylic acid anhydride (5 g, 30.0 mmol), which was dissolved in $CH_2Cl_2$. 1.1 eq of N-(tert-butoxycarbonyl)ethanolamine (5.32 g, 33 mmol) and 10 mol % 4-dimethylaminopyridine (DMAP) were added. After stirring over night, the solution was concentrated. Ether was added to precipitate DMAP salt, and the solution was filtered. This step was repeated until no more DMAP salts precipitated and the pure zwitterion was obtained. The isolated yield was 60-70%.

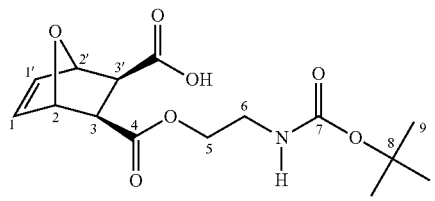 [SMILES: CC(C)(C)OC(=O)NCCOC(=O)[C@H]1C2C=CC(O2)[C@H]1C(=O)O]

$^1$H-NMR (300 MHz, CDCl$_3$): δ=1.41 (s, 9H, H9), 2.83 (m, 2H, H3 & H3'), 3.37 (m, 2H, H6), 4.18 (m, 2H, H5), 5.24 & 5.32 (s, 2H, H2 & H2'), 6.46 (m, 2H, H1 & H1'), 7.5-8.2 (br s, 1H, OH). HR-MS (FAB): calc. 299.31 g/mol. found 272.1 g/mol (M t-Butyl).

1.2—Polymer Synthesis:

The monomer was dissolved in 4 mL dichloromethane, and the respective amount of G3-catalyst (see Table 1 below for details) was dissolved in 1 mL dichloromethane tetrahydrofurane each and subject to three freeze-thaw cycles. The catalyst was added in one shot to the vigorously stirring monomer solution at room temperature under $N_2$. After 30 min, the living polymer chain was end-capped with an excess of ethylvinyl ether (1 mL). The solution was allowed to stir for 2 hours. After evaporation of the solvent and drying, an aliquot of each polymer was taken for GPC and NMR analysis. The product was a brown solid. GPC was performed in THF (polystyrene standards).

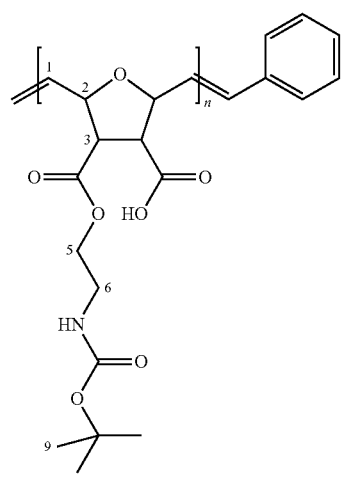

$^1$H-NMR (300 MHz, THF-d$_8$): 1.40 (s, 9H, H9), 3.10 (br m, 2H, H3 & H3'), 3.28 (br m, 2H, H6), 4.07 (br m, 2H, H5), 4.71 (m, 1H, H2 trans), 5.09 (br s, 1H, H2 cis), 5.59 (br s, 1H, NH), 5.91 (br m, 1H, H1 cis) and 6.12 (br m, 1H, H1 trans).

TABLE 1

Experimental parameters for the polymer synthesis

| Sample | $N_{repeat\ units}$ | $M_{n\ Target}$ g mol$^{-1}$ | $M_{Monomer}$ g mol$^{-1}$ | $n_{Monomer}$ mmol | $m_{Monomer}$ mg | $M_{Catalyst}$ g mol$^{-1}$ | $n_{Catalyst}$ mmol | $m_{Catalyst}$ mg |
|---|---|---|---|---|---|---|---|---|
| 1a | 306 | 100.000 | 327.3 | 1.53 | 500 | 726.6 | 0.0051 | 3.7 |
| 1b | 612 | 200.000 | | | | | 0.010 | 1.9 |

1.3—Polymer Deprotection for Solution Testing:

The crude polymer was dissolved in 2 mL dichloromethane. An excess of TFA (2 mL, 2.97 g, 26.0 mmol) was added and the solution was stirred at room temperature over night. The excess acid was removed by azeotropic distillation with dichloromethane (2×15 mL) and methanol (1×15 mL) at the rotary evaporator. The samples were dried in vacuo over night and dissolved in 30 mL Milli-Q water or DMSO depending on solubility. They were dialyzed against Milli-Q water until the conductivity of the water was 0.1 μS after 12 h of dialysis (total dialysis time 4-7 days). The hydrolyzed polymer was then freeze dried.

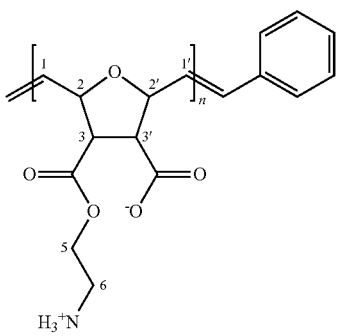

¹H-NMR (300 MHz, DMSO-d₆+D₂O): 3.02 (br m, 2H, H3 & H3'), 3.21 (br m, 2H, H6), 3.70 (br m, 2H, H5), 4.28 (m, 1H, H2 trans), 4.42 (br s, 1H, H2 cis), 5.60 (br m, 1H, H1 cis) and 5.83 (br m, 1H, H1 trans).

1.4—Immobilization of the Antibiofouling Polymer on the Si-Wafer (Silanized as Described Above) as a Monolayer:
i. 50 mg of polymer 1 was dissolved in 2.5 mL of THF yielding a 20 mg mL⁻¹ solution. 0.5 mL of polymer solution was filtered through a 0.45 µm syringe filter and added dropwise to the center of the silanized silicon wafer. It was then spin-coated at 3000 rpm for 120 sec, yielding a 70±5 nm thick polymer film.
ii. The polymer-coated silicon wafer was covalently cross-linked at a wavelength of 250 nm for 30 min using a Strata-linker device (Stratagene). The coated silicon wafer was then rinsed with THF (3×) to remove the excess polymer, and dried under N₂.
iii. The polymer-coated silicon wafer was immersed into a 4 M solution of HCl in dioxane over night. It was the rinsed with isopropanol and ethanol (2×) to remove reaction byproducts, and subject to further characterization.

1.5—Deprotection of Polymer Monolayer.
The functionalized wafer was immersed into 4 M HCl in dioxane for 4-12 hours. It was then washed with diethyl ether, dichloromethane and ethanol and blow dried under a stream of nitrogen.

Characterization:
Film thickness (measured by Ellipsometry):
before deprotection: 10±1 nm
after deprotection: 4±1 nm
Contact angle (static/advancing/receding):
before deprotection: 71±2/73±2/14±2
after deprotection: 54±2/58±2/7±2

Example 2

Surface-Bound Antibiofouling and Antimicrobial Polymer Network 2.1—Polymer Synthesis:
All solvents and reagents were obtained in p.a. or reagent quality from the usual suppliers, unless otherwise specified. The crosslinking agent 3EBP-silane was synthesized as described in the literature (see Example 1) The monomers 2 (R=Methyl to Hexyl or H) were synthesized as described previously (see Lienkamp et al., *Journal of the American Chemical Society* 2008, 130 (30), 9836-9843; Lienkamp et al., *Chemistry—a European Journal* 2009, 15 (44), 11784-11800). The antibiofouling polymer was synthesized as described in example 1. The antimicrobial polymer was synthesized as described in the literature polymer was synthesized as described in the literature (see Lienkamp et al., *Journal of the American Chemical Society* 2008, 130 (30), 9836-9843).

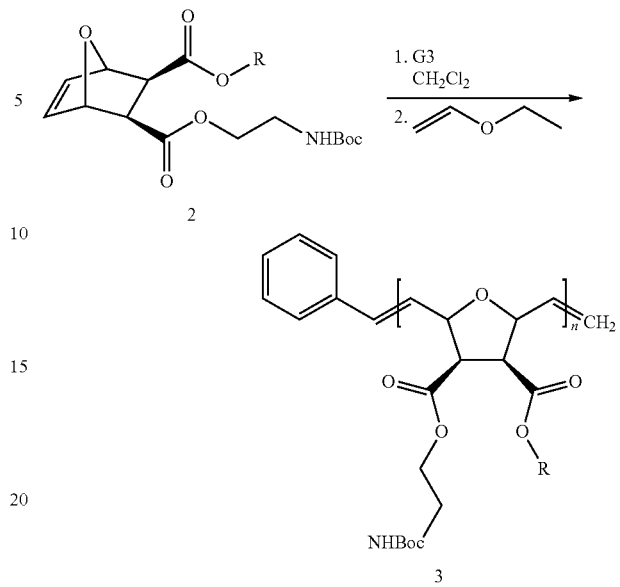

A typical polymerization was performed as follows, where all manipulations were performed under nitrogen using standard Schlenk technique.1 (R=Propyl, 500 mg, 1.35 mmol) was dissolved in 2 mL CH₂Cl₂. Grubbs third generation catalyst (G3, 3.6 mg, 5 µmol) was dissolved in 2 mL CH₂Cl₂ in a second flask and added to the monomer solution. After 30 min, excess ethylvinyl ether (1 mL) was added. The mixture was stirred for 2 hours. The solvent was then evaporated under reduced pressure. The NMR signals of the polymer matched those in the literature. GPC analysis (PSS SDV column, Chloroform, r.t., 1 mL/min) indicated that a polymer with a molecular weight of 120 000 g mol⁻¹ and a polydispersity of 1.24 was obtained.

2.2—Surface-Bound Polymer Network Formation:
A solution of polymer 3 (10 mg/ml), tetrathiol (0.04 mg/ml) and DMPAP (0.01 ml/ml) in a mixture of dichloromethan and toluene (1:1) was produced. This solution was spin-cast on a 3-EBP treated silicon wafer (see 0.3) by spin-coating at 3000 rpm for 2 minutes to yield a thin polymer film. The film was cross-linked at 250 nm for 30 min using a Stratalinker. It was then washed with dichloromethane to remove unattached polymer chains and dried over night under N₂-flow. To activate the antimicrobial function, the film was immersed in HCl (4 M in dioxane) for 12 hours and washed twice with ethanol. It was then dried over night under N₂-flow.

Characterization:
The surface-bound polymer networks in the protected and deprotected form were analyzed using ellipsometry to obtain the layer thickness, contact angle measurement, and atomic force microscopy.

|  |  | SMAMP | | Poly(zwitterion) | |
| --- | --- | --- | --- | --- | --- |
|  |  | protected | deprotected | protected | deprotected |
| Thickness | nm | 70 ± 2 | 60 ± 2 | 65 ± 2 | 57 ± 2 |
| Contact | static | 88 ± 3 | 56 ± 2 | 72 ± 2 | 54 ± 2 |
| angle | advancing | 90 ± 2 | 59 ± 2 | 73 ± 2 | 59 ± 2 |
|  | receding | 38 ± 2 | 14 ± 2 | 14 ± 2 | 7 ± 2 |

2.3—Control Experiment with Low Molecular Weight Polymer.

When a propyl homopolymer with a molecular weight of 50 000 g mol$^{-1}$ was treated similarly to example 2.2, the films obtained could be partially washed away with dichloromethane. This emphasizes the need for high molecular weight for making surface bound monolayers and networks.

Example 3

Self-Patterning Surface-Bound Antibiofouling and Antimicrobial Polymer Networks 3.1—Cross-Linking Solutions:

A propyl homopolymer with a molecular weight of 500 000 g mol$^{-1}$ was synthesized analogously to the description in example 2.1. Monomer 2 (R=Propyl; 1.33 g, 3.59 mmol) was dissolved in 30 mL CH$_2$Cl$_2$. In a second flask, a solution of Grubbs catalyst (4.7 mg, 6.5 mmol) dissolved in 3 mL CH$_2$Cl$_2$ was produced. This solution was added to the first flask. After 30 min, 1 mL ethylvinylether (0.75 g, 10.4 mmol) was added. The mixture was stirred over night. The product was dried under reduced pressure. The respective amount of this polymer was dissolved in the specified amount of dichloromethane; for the cross-linker solutions, the respective amount of 2,2-dimethoxy,2-phenyl-acetophenone (DMPAP), and pentaerythritoltetrakis(3-mercaptopropionate) (tetrathiol) were dissolved in the specified amount of dichloromethane. This yielded solutions 1-4, respectively.

| Solution | Solute | m (solute)/ mg | n (solute)/ mmol | V (solvent)/ mL | c (solute)/ mol L$^{-1}$ |
|---|---|---|---|---|---|
| 1 | Polymer 2 | 101.9 | 0.28 (repeat units) | 5.0 | 0.055 (repeat units) |
| 2 | DMPAP | 2.7 | 0.011 | 10.0 | 0.001 |
|   | Tetrathiol | 128.0 | 0.26 |   | 0.026 |
| 3 | Polymer 2 | 102.1 | 0.28 (repeat units) | 5.0 | 0.055 (repeat units) |
| 4 | DMPAP | 0.9 | 0.004 | 10.0 | 0.0004 |
|   | Tetrathiol | 128.0 | 0.26 |   | 0.026 |

3.2—Polymer Network Formation:

In a typical cross-linking experiment, solutions A-K were prepared according to the recipes below. They were dispensed on the stationary silicon wafer, which had been pre-treated as described above. Immediately afterwards, the wafer was spun with a rotation speed of 2000 rpm for 60 s. The resulting layer was cross-linked by flood exposure at 250 nm for 45 min using a Newport Oriel NUV illumination system MODEL 97000STD4. The wafers were then immersed in dichloromethane for 1 h and dried over night under continuous N$_2$-flow. The resulting layer was characterized by ellipsometry and atomic force microscopy as detailed below.

Solution Recipes:

| Solution | Component | V/mL | m (solute)/ mg | n (solute)/ mmol | V (total)/ mL | c (solute)/ mol L$^{-1}$ |
|---|---|---|---|---|---|---|
| A | Solution 1 | 0.4 | 8.12 | 0.022 | 0.8 | 0.028 |
|   | Solution 2 | 0.4 | Tetrathiol: 5.12 | Tetrathiol: 0.010 |   | Tetrathiol: 0.013 |
|   |   |   | DMPAP: 0.108 | DMPAP: 0.0004 |   | DMPAP: 0.0005 |
|   | DCM | 0.0 |   |   |   |   |
| B | Solution 1 | 0.4 | 8.12 | 0.022 | 0.8 | 0.028 |
|   | Solution 2 | 0.3 | Tetrathiol: 3.84 | Tetrathiol: 0.008 |   | Tetrathiol: 0.010 |
|   |   |   | DMPAP: 0.081 | DMPAP: 0.0003 |   | DMPAP: 0.0004 |
|   | DCM | 0.1 |   |   |   |   |
| C | Solution 1 | 0.4 | 8.12 | 0.022 | 0.8 | 0.028 |
|   | Solution 2 | 0.2 | Tetrathiol: 2.56 | Tetrathiol: 0.005 |   | Tetrathiol: 0.007 |
|   |   |   | DMPAP: 0.054 | DMPAP: 0.0002 |   | DMPAP: 0.0003 |
|   | DCM | 0.2 |   |   |   |   |
| D | Solution 1 | 0.4 | 8.12 | 0.022 | 0.8 | 0.028 |
|   | Solution 2 | 0.1 | Tetrathiol: 1.28 | Tetrathiol: 0.003 |   | Tetrathiol: 0.003 |
|   |   |   | DMPAP: 0.027 | DMPAP: 0.0001 |   | DMPAP: 0.0001 |
|   | DCM | 0.3 |   |   |   |   |

Molar Ratios of the Reaction Solutions:

| Solution | n (1, repeat units)/ mmol | n (tetrathiol)/ mmol | n (DMPAP)/ mmol | Ratio of polymer repeat units: SH units:DMPAP |
|---|---|---|---|---|
| A | 0.022 | 0.010 | 0.0004 | 1:1.9:0.019 |
| B | 0.022 | 0.008 | 0.0003 | 1:1.4:0.014 |
| C | 0.022 | 0.005 | 0.0002 | 1:1.0:0.010 |
| D | 0.022 | 0.003 | 0.0001 | 1:0.5:0.005 |

Characterization:

AFM investigation revealed that instead of a homogeneous film, a porous film with pores of defined size distribution were obtained. The results are summarized below. It is believed that a phase separation of the polymer and the cross-linking solution occurs, combined with dewetting, which leads to a templating effect.

Example 4

Photolithographic Structuring of Surface-Bound Antibiofouling and/or Antimicrobial Polymer Networks 4.1—Polymer 3, with a molecular weight of M=500 000 g mol$^{-1}$, was dissolved in dichloromethane to yield a 40 mg mL$^{-1}$ solution. A stock solution of 120 mg tetrathiol and 2 mg DMPAP in 5 mL dichloromethane was prepared. 0.5 mL of this solution was mixed with 0.5 mL polymer solution.

4.2—Wafer pieces were cleaned with acetone and isopropanol and spun at 3000 rpm. The solution mixture of example 6.1 was added to the rotating sample and spun for 60 sec. The resulting films were covered with a lithographic test mask and flood exposed to UV light using a Newport Oriel NUV illumination system MODEL 97000STD4 without filter. A control film was produced similarly, but without the test mask. Both samples were washed carefully with dichloromethane. The control film had a thickness of 308 nm (determined by ellipsometry). The micrographs of the lithographically structured film are shown in FIG. 1.

Example 5

Surface-Modification of Antimicrobial and/or Antibiofouling Networks by "Grafting onto"

A silicon wafer that has been treated as described in example 2.2 was placed into an oven-dried vial under nitrogen atmosphere. The wafer was then covered with a solution zwitterionic polymer with pentafluorophenol endgroup (6 mg, $1 \cdot 10^{-3}$ mmol, M=6000 g/mol, in 4 mL dichloromethan) that had been prepared analogously to the end-functionalized SMAMP in Madkour et al., *Macromolecules* 2010, 43 (10), 4557-4561. A solution of N,N-dimethylaminopyridine in dichloromethane (1 mL, 0.2 mg/mL, 2 eq.) was added, followed after 2 h by a solution of dicyclohexylcarbodiimid in dichlormethane (1 mL, 0.8 mg/mL, 4 eq.). After 3 days, the wafer was taken out and washed with hexane, DCM, water and ethanol. For deprotection of the Boc-group on the zwitterionic polymer, the wafer was immersed in HCl (4 M in dioxane) for 5 hours and washed twice with ethanol. Finally, the film was dried under $N_2$-flow over night.

Characterization: The surface-bound polymer networks in the protected and deprotected form were analyzed using ellipsometry to obtain the layer thickness, contact angle measurement, and atomic force microscopy.

|  |  | Poly(zwitterion)@ SMAMP | | SMAMP@ Poly(zwitterion) | |
|---|---|---|---|---|---|
|  |  | protected | deprotected | protected | deprotected |
| Thickness | nm | 48 ± 2 | 37 ± 2 |  |  |
| Contact angle: | static | 74 ± 2 | 54 ± 3 |  |  |
|  | advancing | 73 ± 2 | 58 ± 2 |  |  |
|  | receding | 16 ± 2 | 9 ± 2 |  |  |

Example 6

Blending of SMAMPs with Polymers Bearing UV-Crosslinkable Groups and Thermo-Crosslinkable Groups 6.1. SMAMP 3 was mixed in 1:1 weight ratio with polymer 4, a copolymer of N,N-dimethylacrylamide and the UV crosslinker benzophenyl methyl methyacryate (95:5, $M_n$=150 000 g mol$^{-1}$). It was then dissolved in dichloromethane and spin cast onto a 3EBP-functionalized silicon wafer at 3000 rpm for 60 seconds. It was UV irradiated using a stratalinker at 250 nm for 30 min. The resulting polymer film had a thickness of 100 nm, as determined by ellipsometry.

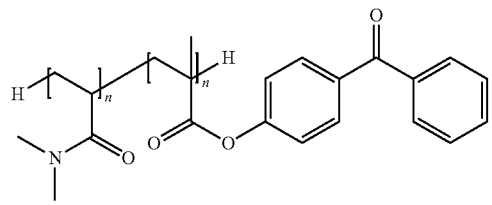

Polymer 4

6.2. The solution described in example 6.1 was solvent cast into a Teflon mold and irradiated for 45 min using a stratalinker at 250 nm. It was then allowed to dry over night. A copolymer blend of SMAMP and polymer 4 was thus obtained.

6.3. SMAMP 3 was mixed in 1:1 weight ratio with polymer 5, a copolymer of N,N-dimethylacrylamide and the thermo crosslinker styrene sulfonic acid azide (95:5, $M_n$=150 000 g mol$^{-1}$). It was then dissolved in dichloromethane and spin cast onto a 3EBP-functionalized silicon wafer at 3000 rpm for 60 seconds. It was heated for 60 min to 120° C. on a hot plate. The resulting polymer film had a thickness of 89 nm, as determined by ellipsometry.

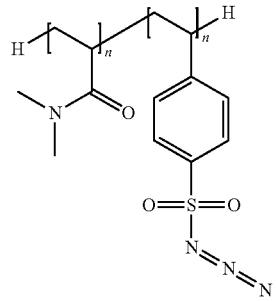

Polymer 5

6.4. The solution described in example 6.3 was solvent cast into a Teflon mold and heated for 60 min at 120° C. It was then allowed to dry over night. A copolymer blend of SMAMP and polymer 5 was thus obtained.

6.5. SMAMP 3 and polymer 5 were co-extruded at 250° C. yielding a granular copolymer blend.

Example 7

Synthesis of Antimicrobial Polymers with Predetermined Break Points (R) for Triggered Release of Active Antimicrobial Agents Monomer 2 with R=propyl (500 mg, 1.53 mmol) was dissolved in 4 mL dichloromethane. 123.3 mg (0.17 mmol) of G3-catalyst were dissolved in 1 mL tetrahydrofurane. Both were subject to three freeze-thaw cycles. The catalyst was added in one shot to the vigorously stirring monomer solution at room temperature under $N_2$. After 10 min, 1.53 mmol of comonomer were added

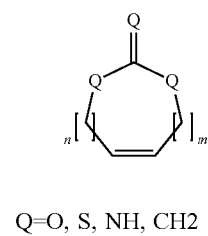

Q=O, S, NH, CH2

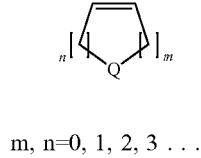

m, n=0, 1, 2, 3 . . .

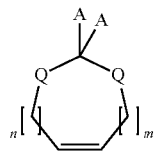

A=H, any aliphatic group, any aromatic group . . . .

The process was repeated 3 times, then 500 mg of monomer 2 where added, and the living polymer chain was quenched with ethyl vinyl ether, yielding a polymer with the sequence (SMAMP-X)$_n$-SMAMP, where n=3.

The thus created polymer with intended break points (R) at X can then be used in either of the formulations described above (examples 2-5). It is then treated with trifluoroacetic acid, HCl, or thermally, to yield the active antimicrobial function.

Upon addition of 6 N HCl or an esterase, the comonomer is hydrolyzed, and low molecular weight SMAMPs are released into any solution surrounding the material.

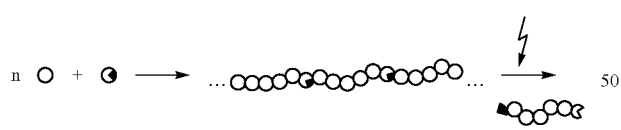

The invention claimed is:

1. Substrate comprising covalently attached to the surface of the substrate a crosslinked network of antimicrobial or antibiofouling polymers, wherein covalent attachment to the surface of the substrate and crosslinking of the network has been carried out simultaneously, the antimicrobial or antibiofouling polymers comprising a molecular weight of more than 30,000 g mol$^{-1}$ and as a repeat unit a) for the antimicrobial polymer, a structure according to at least one of the following formulae:

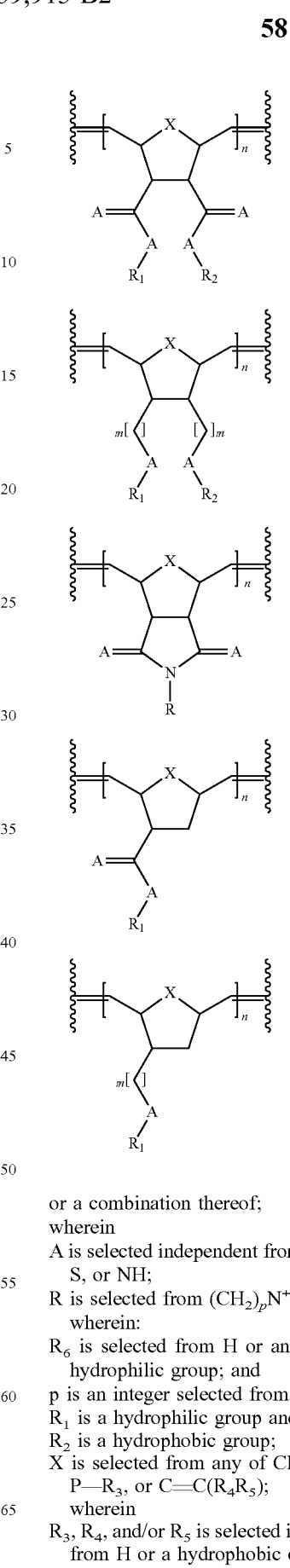

or a combination thereof;
wherein
A is selected independent from each other from any of O, S, or NH;
R is selected from (CH$_2$)$_p$N$^+$(R$_6$)$_3$
wherein:
R$_6$ is selected from H or an uncharged hydrophobic or hydrophilic group; and
p is an integer selected from a range of 1 to 10;
R$_1$ is a hydrophilic group and carries a positive charge;
R$_2$ is a hydrophobic group;
X is selected from any of CH$_2$, CH$_2$CH$_2$, O, S, N—R$_3$, P—R$_3$, or C=C(R$_4$R$_5$);
wherein
R$_3$, R$_4$, and/or R$_5$ is selected independent from each other from H or a hydrophobic or hydrophilic group;

n is an integer selected from a range of 10 to 2500;
m is an integer selected from a range of 0 to 20; and
wherein a net charge of all positive and negative charges per repeat unit of any of formulae (Ia), (Ib), (Ic), (Id) and/or (Ie) in their deprotected form is greater than 0;
b) for the antibiofouling polymer, a structure according to at least one of the following:

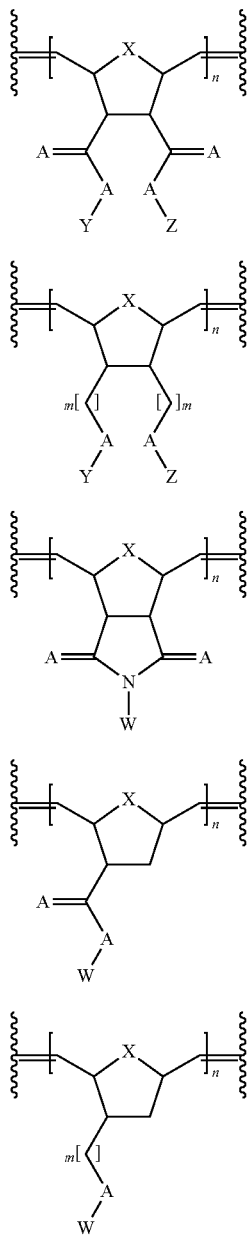

(IIa)

(IIb)

(IIc)

(IId)

(IIe)

or a combination thereof;
wherein
A is selected independent from each other from any of O, S, or NH;
W is selected from any of $(CH_2)_q N^+(R_{11}R_{12}R_{13})$, or $(CH_2)_q O-PO_2^- -(CH_2)_r N^+(R_{14}R_{15}R_{16})$,
wherein
$R_{11}$, $R_{12}$ is independent from each other an uncharged hydrophobic or hydrophilic group, and $R_{13}$ is selected from any of $(CH_2)_r CO_2^-$, $(CH_2)_r SO_3^-$, $(CH_2)_r-O-SO_3^-$, $(CH_2)_r-O-PO_3^-$, $(CH_2)_r PO_3^-$, $R_{14}$, $R_{15}$, $R_{16}$, is independent from each other H or a hydrophobic or hydrophilic group, q, r are integers, each independently selected from a range of 1 to 10;

X is selected from any of $CH_2$; $CH_2CH_2$; O; S; N—$R_9$; N—$R_{10}$; N—W; P—$R_9$; P—$R_{10}$; P—W; $N^+(R_9R_9)$; $N^+(R_9R_{10})$; $N^+(R_9W)$; $N^+(R_{10}W)$; $N^+(R_{10}R_{10})$; $N^+(WW)$; C=$CH_2$; C=$C(R_9R_9)$; C=$C(R_9R_{10})$, C=$C(R_9W)$; C=$C(R_{10}W)$, C=$C(R_{10}R_{10})$, C=C(WW), wherein:
$R_9$ is selected independent from each other from a hydrophobic or hydrophilic group, $R_{10}$ is selected independent from each other from any of $(CH_2)_r CO_2^-$, $(CH_2)_r SO_3^-$, $(CH_2)_r-O-SO_3^-$, $(CH_2)_r PO_3^-$, $(CH_2)_r PO_3^-$; and r is an integer selected from a range of 1 to 10;

Y is selected from W or any hydrophilic or hydrophobic group

Z is selected from W or any hydrophilic or hydrophobic group n is an integer selected from a range of 10 to 2500;

m is an integer selected from a range of 0 to 20; and wherein a net charge of all positive and negative charges per repeat unit of any of formulae (IIa), (IIb), (IIc), (IId) and/or (IIe) in their deprotected form is 0;

wherein the surface of the substrate is selected from an inorganic surface, or an organic surface.

2. Substrate according to claim 1, wherein the antimicrobial or antibiofouling polymers of the network are cross-linked using a di-, tri-, tetra- or higher functional crosslinker.

3. Substrate according to claim 2, wherein the antimicrobial or antibiofouling polymers of the network are cross-linked using a di-, tri-, tetra- or higher functional thiol crosslinker.

4. Substrate according to claim 1, wherein the antimicrobial or antibiofouling polymers of the network are further modified via grafting onto with an antimicrobial or antibiofouling polymer selected from

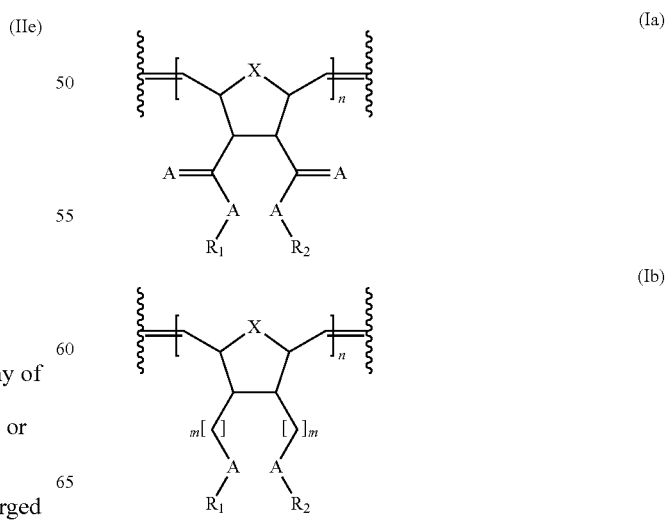

(Ia)

(Ib)

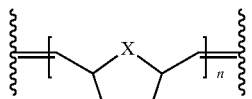
(Ic)

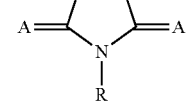
(Id)

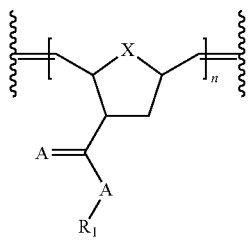
(Ie)

wherein
A is selected independent from each other from any of O, S, or NH;
R is selected from $(CH_2)_p\ N^+(R_6)_3$
wherein:
$R_6$ is selected from H or an uncharged hydrophobic or hydrophilic group; and
p is an integer selected from a range of 1 to 10;
$R_1$ is a hydrophilic group and carries a positive charge;
$R_2$ is a hydrophobic group;
X is selected from any of $CH_2$, $CH_2CH_2$, O, S, N—$R_3$, P—$R_3$, or C=C($R_4R_5$);
wherein
$R_3$, $R_4$, and/or $R_5$ is selected independent from each other from H or a hydrophobic or hydrophilic group;
n is an integer selected from a range of 10 to 2500;
m is an integer selected from a range of 0 to 20; and
wherein a net charge of all positive and negative charges per repeat unit of any of formulae (Ia), (Ib), (Ic), (Id) and/or (Ie) in their deprotected form is greater than 0;

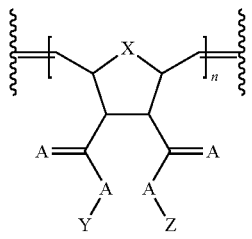
(IIa)

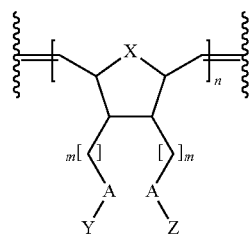
(IIb)

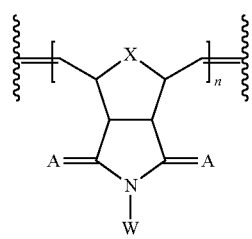
(IIc)

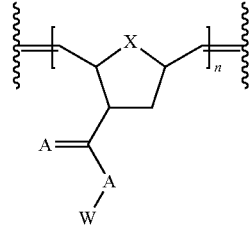
(IId)

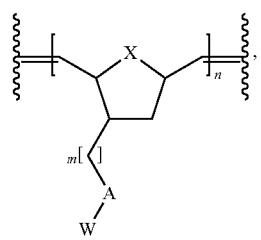
(IIe)

wherein
A is selected independent from each other from any of O, S, or NH;
W is selected from any of $(CH_2)_qN^+(R_{11}R_{12}R_{13})$, or $(CH_2)_qO$—$PO_2^-$—$(CH_2)_rN^+(R_{14}R_{15}R_{16})$,
wherein
$R_{11}$, $R_{12}$ is independent from each other an uncharged hydrophobic or hydrophilic group, and
$R_{13}$ is selected from any of $(CH_2)_rCO_2^-$, $(CH_2)_rSO_3^-$, $(CH_2)_r$—O—$SO_3^-$, $(CH_2)_r$—O—$PO_3^-$, $(CH_2)_r PO_3^-$,
$R_{14}$, $R_{15}$, $R_{16}$, is independent from each other H or a hydrophobic or hydrophilic group,
q, r are integers, each independently selected from a range of 1 to 10;
X is selected from any of $CH_2$; $CH_2CH_2$; O; S; N—$R_9$; N—$R_{10}$; N—W; P—$R_9$; P—$R_{10}$; P—W; $N^+(R_9R_9)$; $N^+(R_9R_{10})$; $N^+(R_9W)$; $N^+(R_{10}W)$; $N^+(R_{10}R_{10})$; $N^+(WW)$; C=$CH_2$; C=C($R_9R_9$); C=C($R_9R_{10}$), C=C($R_9W$); C=C($R_{10}W$), C=C($R_{10}R_{10}$), C=C (WW),
wherein:
$R_9$ is selected independent from each other from a hydrophobic or hydrophilic group,
$R_{10}$ is selected independent from each other from any of $(CH_2)_rCO_2^-$; $(CH_2)_rSO_3^-$, $(CH_2)_r$—O—$SO_3^-$, $(CH_2)_rPO_3^-$, $(CH_2)_rPO_3^-$; and
r is an integer selected from a range of 1 to 10;

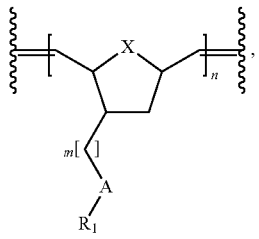

Y is selected from W or any hydrophilic or hydrophobic group

Z is selected from W or any hydrophilic or hydrophobic group n is an integer selected from a range of 10 to 2500;

m is an integer selected from a range of 0 to 20; and wherein a net charge of all positive and negative charges per repeat unit of any of formulae (IIa), (IIb), (IIc), (IId) and/or (IIe) in their deprotected form is 0.

5. Substrate according to claim 1, wherein a structure of the network of antimicrobial or antibiofouling polymers comprises pores having a width of about 50-500 nm.

6. Substrate according to claim 1, wherein the crosslinked network formed by the antimicrobial or antibiofouling polymers comprises a thickness of about 10 nm to about 1000 μm.

7. Substrate according to claim 1, wherein the crosslinked network formed by the antimicrobial or antibiofouling polymers comprises predefined breaking points.

8. Substrate according to claim 1, wherein the crosslinked network of antimicrobial or antibiofouling polymers is micro- or nano-structured according to a defined pattern.

9. Substrate according to claim 1, wherein the surface of the substrate is a polymeric surface.

10. Substrate comprising covalently attached a crosslinked network of antibiofouling polyzwitterionic polymers, the antibiofouling polymers of the network comprising a molecular weight of more than 10,000 g mol$^{-1}$ and as a repeat unit a structure according to at least one formula (IIa):

(IIa)

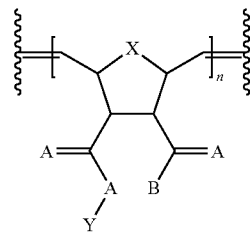

wherein

A is selected from O;

X is selected from O;

Y is selected from the group

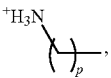

wherein p is an integer selected from a range selected from 1-10;

B is O$^-$ or OH;

n is an integer selected from a range of 10 to 2500;

wherein a net charge of all positive and negative charges per repeat unit of formula (IIa) in its deprotected form is 0.

11. Substrate according to claim 10, wherein the antibiofouling polymer has as a repeat unit a structure according to the following formula:

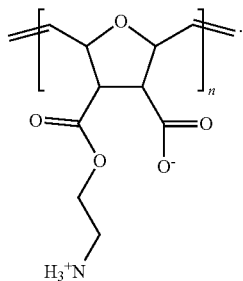

* * * * *